United States Patent [19]
Zebala

[11] Patent Number: 6,159,681
[45] Date of Patent: Dec. 12, 2000

[54] LIGHT-MEDIATED METHOD AND APPARATUS FOR THE REGIONAL ANALYSIS OF BIOLOGIC MATERIAL

[75] Inventor: John A. Zebala, Redmond, Wash.

[73] Assignee: Syntrix Biochip, Inc., Redmond, Wash.

[21] Appl. No.: 09/322,060

[22] Filed: May 27, 1999

Related U.S. Application Data

[63] Continuation-in-part of application No. 09/085,302, May 27, 1998, abandoned.
[60] Provisional application No. 60/048,027, May 28, 1997.
[51] Int. Cl.[7] .............................. C12Q 1/00; C12Q 1/68; G01N 33/53
[52] U.S. Cl. ............... 435/4; 435/5; 435/6; 435/7.1; 435/7.2; 435/7.21; 435/7.71; 435/40.5; 435/40.51; 435/176; 430/56; 430/60; 436/518
[58] Field of Search ............... 435/4, 5, 6, 7.1, 435/7.2, 7.21, 7.71, 40.5, 40.52, 176; 430/56, 60; 436/518

[56] References Cited

U.S. PATENT DOCUMENTS

| | | |
|---|---|---|
| 4,415,405 | 11/1983 | Ruddle et al. .......................... 156/645 |
| 5,128,230 | 7/1992 | Templeton et al. . |
| 5,212,050 | 5/1993 | Mier et al. . |
| 5,349,436 | 9/1994 | Fisch . |
| 5,466,575 | 11/1995 | Cozette et al. . |
| 5,491,097 | 2/1996 | Ribi et al. . |
| 5,510,270 | 4/1996 | Fodor et al. ............................. 436/518 |

FOREIGN PATENT DOCUMENTS

| | | |
|---|---|---|
| 402 718 A1 | 12/1990 | European Pat. Off. . |
| 4-040890 | 2/1992 | Japan . |
| 10-215862 | 3/1997 | Japan . |
| WO98/33902 | 8/1998 | WIPO . |

OTHER PUBLICATIONS

Flounders et al. (1997). Patterning of immobilized antibody layers via photolithography and oxygen plasma exposure. Biosensors and Bioelectronics. 12(6):447–456.

*Primary Examiner*—Christopher L. Chin
*Assistant Examiner*—Minh-Quan K. Pham
*Attorney, Agent, or Firm*—Seed Intellectual Property Law Group PLLC

[57] ABSTRACT

Compositions and methods are provided for performing regional analysis of biologic materials. The methods provided herein employ a photoresist layer that is established over a biologic material (which may be immobilized on a substrate). Regions of interest are selected and irradiated to expose specific regions of biologic material. Exposed biologic material may then be selectively analyzed using any of a variety of analytic methods.

49 Claims, 15 Drawing Sheets

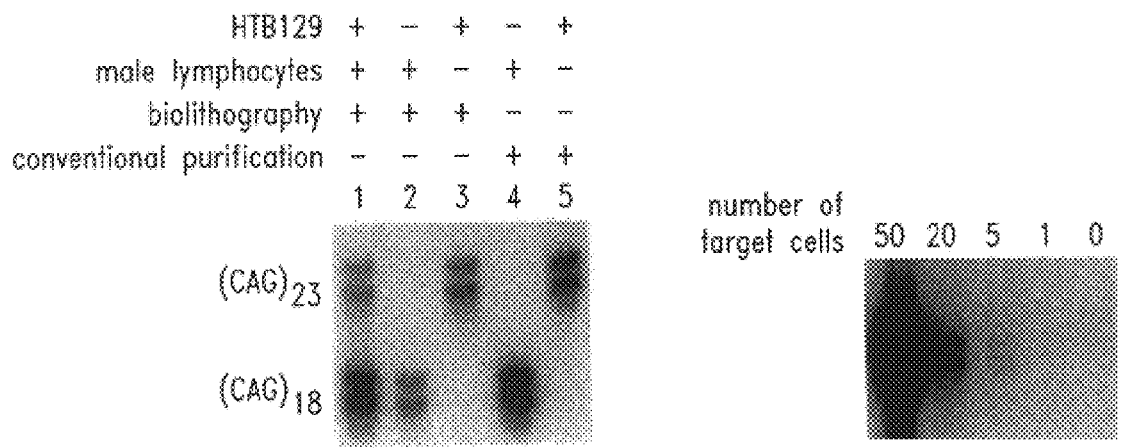
*Fig. 10*
*Fig. 12*
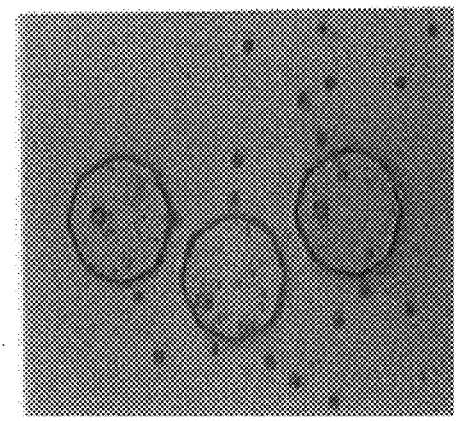
Before protease
*Fig. 11A*
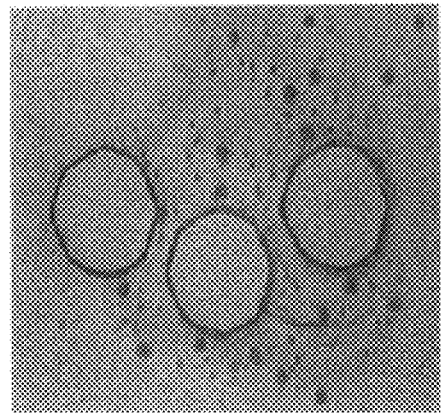
After protease
*Fig. 11B*

Case 1196

Case 1639 biolithography  + + + −
microdissection − − − +
                N C C C

Case 2767

| Marker | Xq27.3 DXS1123 | MECP2 DXS15 | Xq27.3 DXS1113 |

N D C  N D C  N D C

LIGHT-MEDIATED METHOD AND APPARATUS FOR THE REGIONAL ANALYSIS OF BIOLOGIC MATERIAL

CROSS REFERENCE TO RELATED APPLICATION

This application is a continuation-in-part of U.S. patent application Ser. No. 09/085,302 filed May 27, 1998, now abandoned, which claims the benefit of U.S. Provisional Patent Application No 60/048,027 filed May 28, 1997, currently pending.

TECHNICAL FIELD

The present invention relates generally to methods for regional analysis of biologic materials. The invention is more particularly related to methods employing photoresist compositions and selective irradiation to provide for the precise and specific analysis of discrete regions of a biologic material.

BACKGROUND OF THE INVENTION

The relationship between position and chemical composition is a fundamental issue in the study of biologic systems. For example, position-composition relationiships are important in understanding mosaicism, the clonal evolution of cancer, tissue methylation patterns, cell-cell communication, tissue-specific gene expression, developmental gene expression and cell-specific infection (e.g., viral). At the subcellular level, an understanding of such relationships is critical for gaining insight into the mechanisms by which how chromosomes and other molecules form the architecture of the cell itself. Numerous in situ methods are presently available to study position-composition relationships, including immunocytochemistry (i.e., using antibodies to detect antigen compositions), fluorescence in situ hybridization (i.e., hybridization of nucleic acid probes to detect nucleic acid compositions) and in situ PCR (i.e., locally amplifying a target sequence followed by hybridization with labeled probes). In situ methods detect position-composition relationships by directly contacting biologic material, usually while on a glass slide, with an assay mixture for a particular composition. The in situ assay mixture produces a visible product which co-localizes with the composition it detects, revealing position-composition relationships by visual inspection. Currently available methods have significant limitations including the types of compositions that can be detected, the sensitivity and specificity of detection, the number of assays that can be performed on the same biologic material, the need for significant human interpretation, and the difficulty in automating process steps.

In contrast, analytic methods detect one or more compositions with an assay whose products homogeneously distribute in the assay mixture. The average content of all compositions present in the sample is detected rather than specific position-composition relationships. Despite this drawback, the advantages of analytic methods are significant including a wide variety of detectable compositions, outstanding sensitivity and specificity, multiple and often simultaneous assays on the same material, and the ease by which process and interpretation steps may be automated.

To facilitate the study of biological systems, methods that detect position-composition relationships using the advantages of analytic methods are desirable. A major obstacle to the development of such methods is the need to precisely isolate material in positions of interest from the vast majority of remaining biologic material. In attempts to overcome this obstacle, several physical dissection methods have been described including gross dissection of frozen tissue blocks to enrich for specific cell populations (see Fearon et al., *Science* 238:193, 1987 and Radford et al., *Cancer Res.* 53:2947, 1993), and "touch preparations" of frozen tissue specimens (see Kovach et al., *J. Natl. Cancer Inst.* 83:1004, 1991). These methods do not visualize regions of interest microscopically. Selection capabilities are therefore crude, resulting in significant sample contamination. Microdissection using a dissecting microscope has been described providing for better isolation of selected material (see Emmert-Buck et al., *Am. J. Pathol.* 145:1285, 1994; Zhuang et al., *Am. J. Pathol.* 146:620, 1995 and Noguchi et al., *Cancer Res.* 54:1849, 1994). However, microdissection is highly labor intensive and difficult to automate.

Others have attempted to define position-composition relationships in neoplastic cells by growing xenografts, free of infiltrating nonneoplastic cells, in athymic nude mice (see Schutke et al., *Proc. Natl. Acad. Sci. USA* 92:5950, 1995 and Caldas et al., *Nature Genet.* 8:27, 1994). However, this method results in xenograft contamination with up to 50% nonneoplastic murine cells, requires weeks for growth, cannot be automated, applies only to autonomously growing cells, and may artifactually alter the composition of cells through the introduction of mutations in the growing xenograft.

An ultraviolet light-mediated method has been described which destroys unwanted genetic material with ultraviolet irradiation except where it has been manually ink-stained with an ink-pen (see Shibata et al., *Am. J. Pathol.* 141:539, 1992). This method, known as selective ultraviolet radiation fractionation (i.e., SURF), suffers from crude resolution dictated by the size of the ink-pen and requires up to 30 minutes of ultraviolet exposure to destroy unwanted material. Biomolecules are also limited to those sensitive to ultraviolet light. Other disadvantages include the need to transfer the material to a tube (either with or without the underlying substrate), the manual application of ink, the difficulty of automating process steps, and a mixture typically containing irradiated material in vast abundance. The latter can contribute to inhibiting various analytic methods including sensitive amplification methods such as PCR.

Laser capture microdissection (LCM) is a recently described method that utilizes a transparent thermoplastic film (ethylene vinyl acetate, EVA) to capture cells from glass slides under direct visualization (see Emmert-Buck et al., *Science* 274:998, 1996). EVA is applied to the surface of a tissue section placed on a glass slide and irradiated with a carbon dioxide laser using infrared radiation. The laser energy is absorbed by the film which adheres to the underlying selected cells, which are selectively procured when the film is removed. Drawbacks of LCM include less than 100% transfer of cells to the EVA film, a glass surface that must be specially prepared so as to facilitate tissue lift-off, and a ragged border between irradiated and non-irradiated regions (i.e., low contrast). Because the entire EVA film is transferred from the slide surface to a reaction tube, there is the potential for contamination of the non-irradiated EVA with tissue fragments. The latter is a significant disadvantage when sensitive amplification methods for detection are employed (e.g., PCR). Also, cumbersome automation and robotics are required in the transfer process resulting in a high system cost. Another disadvantage is a resolution limited by the wavelength of the infrared laser (~10 microns) which precludes microdissection of subcellular components.

It has long been known to immobilize active biomolecules into thin films of poly (vinyl) pyrrolidone (PVP), PVA and protein (see Hanazato, *Anal. Chim. Acta* 193:87, 1987 describing the use of negative photoresists for photopatterning thin films containing biomolecules for the purpose of producing biosensors), Takatsu and Moriizumi, *Sensor and Actuators* 11:309, 1987; Moriizumi and Miyahara, *Sensors and Actuators* 7:1, 1985 and Ichimura, U.S. Pat. No 4,272,620 (describing the incorporation of enzymes into the photosensitive mixtures consisting of poly(vinyl alcohol) (PVA) and styrylpyridinium or stilbazolium salt); and Cozzette, U.S. Pat. No. 5,200,051 (describing a photoformable proteinaceous matrix that behaves as a negative photoresist). However, it has been believed that biologic material is relatively labile and therefore incompatible with the direct application of photoresist because such processing commonly includes exposure to organic chemicals, strong acids, strong bases ultraviolet light, and reactive chemical species in the photoresist as generated by light (see Cozzette, U.S. Pat. Nos. 5,200,051 and 5,466,575).

Accordingly, there is a need in the art for improved methods for regional analysis of biologic materials. In particular, methods are needed to detect position-composition relationships using analytic methods. The present invention fulfills these needs and further provides other related advantages.

SUMMARY OF THE INVENTION

Briefly stated, the present invention provides compositions and methods for regional analysis of biologic materials. Within certain embodiments, the present invention provides methods for analyzing one or more discrete regions of a biologic material, comprising the steps of: (a) irradiating photoresist coated on a first region of a biologic material, wherein the biologic material is immobilized on a substrate, such that: (i) photoresist coated on the first region is substantially removed and photoresist coated on a second region of the biologic material is not substantially removed, resulting in exposed biologic material in the first region; or (ii) photoresist coated on a second region is substantially removed and photoresist coated on the first region of the biologic material is not substantially removed, resulting in exposed biologic material in the second region; and (b) determining the presence or absence of a substance of interest in the exposed biologic material; and therefrom analyzing a discrete region of the biologic material for the presence or absence of a substance of interest. In certain embodiments, the photoresist is a positive photoresist, and the exposed biologic material is in the first region. Within other embodiments, the photoresist is a negative photoresist, and wherein the exposed biologic material is in the second region. Step (b) may be performed using any of a variety of analytical techniques, such as those in which the exposed biologic material is contacted with a detection reagent that generates a detectable response indicative of the presence or absence of a substance of interest in the exposed biologic material; and a response generated by the detection reagent is detected. Detection reagents may comprise, for example, one or more of an antibody, nucleic acid sequence or enzyme and/or a marker such as a chromophor, fluorophor or radionuclide. Other analytical techniques include electrophoresis, chromatography, mass spectrometry, DNA sequencing, peptide sequencing, nucleic acid hybridization and PCR. The applied irradiation may be, for example, coherent light, incoherent light, x-ray light, ultraviolet light, visible light or infrared light.

Within further aspects, the present invention provides methods for analyzing a discrete region of a biologic material, comprising the steps of: (a) irradiating photoresist coated on a first region of a biologic material, wherein the biologic material is immobilized on a substrate, such that: (i) photoresist coated on the first region is substantially removed and photoresist coated on a second region of the biologic material is not substantially removed, resulting in exposed biologic material in the first region; or (ii) photoresist coated on a second region is substantially removed and photoresist coated on the first region of the biologic material is not substantially removed, resulting in exposed biologic material in the second region; and (b) contacting the exposed biologic material with an ablative agent, such that a substance of interest is not detectable in the exposed biologic material; (c) substantially removing remaining photoresist, exposing remaining biologic material, and (d) determining the presence or absence of a substance of interest in the remaining biologic material; and therefrom analyzing a discrete region of the biologic material for the presence or absence of a substance of interest. Ablative agents include, for example, oxidants, free radicals, non-specific nucleases, non-specific ribonucleases, peptide nucleic acid clamps, high energy particles, extremes of radiation, ultraviolet irradiation and combinations thereof.

The present invention further provides, within other aspects, biologic material immobilized on a substrate, wherein at least one region of the biologic material is coated with a photoresist and at least one region of the biologic material is not coated with a photoresist. Within certain aspects, the biologic material is selected from the group consisting of biological tissues, cells, viruses, nucleic acid molecules, peptide nucleic acids, polysaccharides, monosaccharides, lectins and lipids. Within other such aspects, the biologic material is covalently linked to the substrate. Within still further such aspects, the biologic material consists of compounds that comprise molecules selected from the group consisting of nucleic acid molecules, peptide nucleic acids, polysaccharides, monosaccharides, proteins, peptides, lectins and lipids; and the compounds are immobilized by way of linkers, wherein at least 80% of the linkers are separated from other linkers by a distance greater than the diameter of the immobilized compounds. Within certain embodiments or any of the above aspects, at least 100 separate regions of biologic material are exposed (i.e., not coated with photoresist). Within other embodiments, at least 10,000 separate regions of biologic material are exposed.

Within other aspects, the present invention provides an apparatus for targeting irradiation to a biologic material on a substrate, the apparatus comprising (a) a body capable of immobilizing a substrate; (b) a first electromagnetic radiation source that generates a first radiation; (c) first optics that transform the first radiation to a first geometry having a first focal plane; (d) collection optics that receive response radiation from an immobilized substrate; (e) a detector that generates a signal proportional to the amount of radiation received by the collection optics, such that the signal represents an image associated with an immobilized substrate: (f) a second electromagnetic radiation source that generates a second radiation that differs substantially in wavelength from the first radiation; (g) second optics for transforming the second radiation to a second Geometry having a second focal plane; and (h) a focuser that controls the height of the first and second focal planes, relative to an immobilized substrate. The second electromagnetic radiation source may be, for example, a mercury lamp. The apparatus may further comprise an attenuator, such as a shutter, that blocks transfer of second radiation to an immobilized substrate. Alternatively, or in addition, the apparatus may further comprise a processor for processing and storing signal from the detector and coordinating the attenuator and the focuser to permit irradiation of a substrate at the plurality of defined regions.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 10 is an autoradiogram demonstrating specificity of target selection. The "+" symbols in each lane indicate which cells DNA was purified from and the purification method used. Lanes 4 and 5 represent positive controls (in which DNA was purified using conventional methods).

FIGS. 11A and 11B are photographs demonstrating specificity of target selection. FIG. 11A shows destained male lymphocytes. FIG. 11B shows the cells after the addition of extraction solution. Irradiated regions are indicated by the three roughly circular regions.

FIG. 12 is an autoradiogram demonstrating sensitivity of target selection. DNA was extracted from the number of male lymphocytes indicated, PCR amplified, electrophoresed and autoradiographed.

FIG. 14A shows the results from breast cancer case 3413 and FIG. 14B shows the results from breast cancer case 2767. In each case, incubation with methylation-sensitive restriction enzymes is indicated by the "+." DNA was isolated from breast epithelium, squamous epithelium, smooth muscle, lymphoid tissue, vasculature, ductal carcinoma in situ (DCIS, a pre-malignant condition), and nests of primary breast cancer, as indicated.

DETAILED DESCRIPTION OF THE INVENTION

Figure 1:
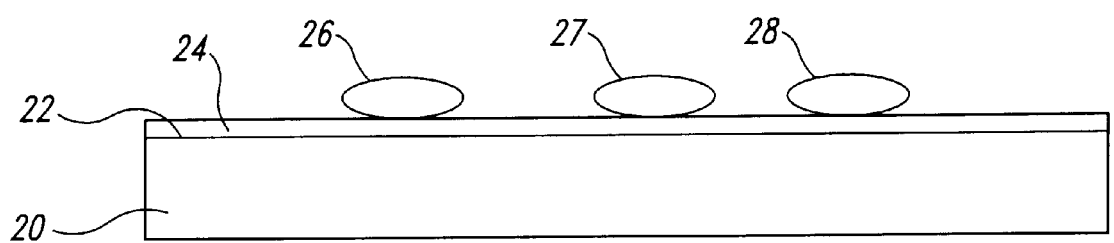
FIG. 1 is a cross-section diagram illustrating the application of biologic material 26, 27 and 28 to a substrate 20 having a surface 22 with linkers 24 attached thereto.
Figure 2:
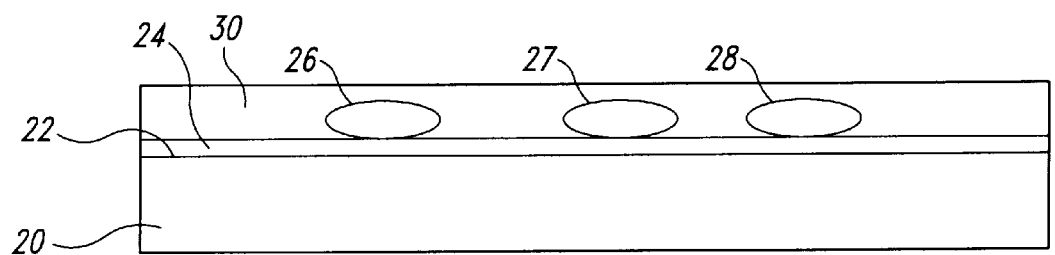
FIG. 2 is a cross-section diagram illustrating the application of a positive photoresist 30 to biologic material 26, 27 and 28 immobilized via linkers 24 to a surface 22 of a substrate 20.

As noted above, the present invention is generally directed to the use of photoresists to provide for precise and specific analysis of discrete regions of a biologic material. Briefly, a photoresist layer is established over a biologic material (which may be immobilized on a substrate). Using an irradiation-targeting device, the biologic material may be visualized microscopically by illumination with a light substantially non-reactive toward the photoresist. Regions of interest are selected and irradiated with a light that is reactive with the photoresist. Following irradiation, photoresist may be contacted with a developer so as to expose biologic material in discrete regions. Exposed biologic material may then be selectively analyzed using any of a variety of analytic methods.

The present invention is based, in part, on the discovery that photoresists may be directly applied to biologic material to facilitate analyses of discrete regions. The methods provided herein are capable of targeting analyses to small and precisely known regions. It is therefore possible to determine position-composition relationships with a high degree of accuracy Methods provided herein further display the advantages of analytic methods including detection of a wide variety of compositions, outstanding sensitivity and specificity, multiple and often simultaneous assays on the same material, and the ease by which process and interpretation steps may be automated.

The present invention may be applied, for example, in any of a variety of fields that require precise analysis of biomolecules in discrete regions of biologic material. For example, one embodiment of the invention provides a method and apparatus for isolating and analyzing DNA from targeted subpopulations of cells. Such applications exist in the field of cancer diagnostics, where the alteration of genetic material in tumors is often obscured by the presence of contaminating normal cells. Using methods provided herein, tumor cells may be exposed exclusively. Other applications may be found in the basic sciences including studies of mosaics, tissue-specific methylation patterns, cell communication, tissue-specific gene expression, developmental gene expression, transgenic gene expression and subcellular position-composition relationships (e.g., chromosome structure in the interphase nucleus and physical gene mapping). The present methods may further be used to assess the biodistribution or bioaccumulation of pharmacologic or toxicologic agents including medicinal agents, pesticides, herbicides and other environmental compounds, toxins and pollutants. Yet another application, described in greater detail below, is the facilitation of screens to detect receptor-ligand interactions.

Other applications of the methods provided herein include providing a direct interface between clinical samples and the "active" surface of DNA-chips (see U.S. Pat. Nos. Brennan, 5,474,796; Pirrung et al., U.S. Pat. No. 5,143,854; McGall et al., U.S. Pat. No. 5,412,087; Fodor et al., U.S. Pat. No. 5,445,934 and Fodor et al., U.S. Pat. No. 5,510,270). In many cases, it may be desirable to restrict the active surface to specific cells in the sample. Further applications include providing the appropriate material for comparative genomic hybridization (CGH); a method confounded by excessive normal cells (see Kallioniemi et al., Science (1992) 258:818). Still further applications include intentional ablation of specific regions in a biologic material, production of molecular-electronic devices, and immobilization of labeled or unlabeled cells, proteins, antibodies, lectins, nucleic acids, nucleic acid probes, polysaccharides and the like in a pattern on a surface via molecular recognition of the exposed biologic material.

GLOSSARY

Prior to setting forth the invention in detail, it may be helpful to an understanding thereof to set forth definitions of certain terms that will be used hereinafter.

"Ablation" refers to the alteration of a portion or all of biologic material, such that a substance of interest is no longer detectable within an assay that would, in the absence of ablation, provide a detectable response. Such alteration may encompass substantially complete destruction by, for example, extreme radiation such as from an excimer laser or reactive ion etch system. Alternatively, the alteration may be relatively mild, resulting in only chemical and/or physical modifications (which may be specific or nonspecific) of molecules in the biologic material. The magnitude of the alteration which must be applied to eliminate an expected detectable response will be readily determined by testing a given alteration at various magnitudes against a representative substance of interest and determining at what magnitude there is no longer a detectable response.

An "ablative agent" is any treatment that results in ablation. "Ablative agents" include, but are not limited to, oxidants, free radicals, non-specific nucleases, non-specific ribonucleases, peptide nucleic acid clamps, high energy particles, extremes of radiation, ultrasonic energy, high pressure liquids, ultraviolet irradiation and combinations thereof.

An "acid labile group" is a portion of a molecule that is cleaved upon exposure to a particular acidic pH.

"Amplification" refers to a detectable increase in the number of copies of a particular nucleic acid fragment or other biologic molecule, usually resulting from an enzymatic reaction such as the polymerase chain reaction (PCR), ligase chain reaction (see Barany et al., U.S. Pat. No. 5,494,810), or a self-sustained sequence reaction (see Guatelli et al., Proc. Natl. Acad. Sci. USA (1990) 87: 1874).

"Analytic methods" refer to the collection of assay techniques available to those skilled in the art that do not provide, by themselves, a position-composition relationship for a given biologic material. Analytic methods include techniques for detecting a specific known compound, as well as techniques for identifying an unknown substance. Representative analytic methods include electrophoresis, chromatography, mass spectrometry, chromogenic or fluorescent enzyme or antibody assays, restriction enzyme digestion, nucleic acid or peptide polymerization, DNA sequencing, peptide sequencing, ligation, PCR, labeling, cloning, hybridization, DNA and RNA purification methods, and autoradiography. Other available analytic methods will be readily apparent to those skilled in the art.

"Analysis" refers to the application of "analytic methods" to "biologic material."

"Analytic assay mixture" refers to the mixture contacting the surface of biologic material in an "analytic method". This is usually a liquid mixture but may also be a mixture of high energy particles or radiation. See "analytic method" above.

Two molecules are said to "bind" if they associate non-covalently such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art. A first molecule is said to "specifically bind" relative to a second unrelated molecule if the ratio of the first molecule's binding constant to the second molecule's binding constant is greater than 2.

A "biologic material" may be any tissue(s), cell(s), virus(es) or portions thereof (e.g., organelles and membranes and fragments thereof). A biologic material may be one or more molecules of a type or types found in nature (e.g., nucleic acid molecules, proteins, peptides, antibodies, polysaccharides, monosaccharides, lectins and lipids). Other molecules included within the scope of "biologic materials" are nonnaturally-occurring nucleobase polymers as defined herein, which mimic naturally occurring nucleic acid molecules, but contain nucleobases linked by a backbone that is not found in nature.

A photoresist is "coated" on a biologic material if the photoresist forms a continuous layer such that the contour height over all points of the biologic material is greater than the contour height of the material alone. For example, a paraffinized tissue slice uniformly measuring 5 microns in thickness will require a photoresist layer such that the total thickness of tissue and photoresist is greater than 5 microns in thickness in order to be coated. The thickness and continuity of the photoresist layer is sufficient to prevent detectable contact of the underlying biologic material with an ablative agent or detection reagent, as described herein.

Preferably, the contour height of the photoresist exceeds the contour height of the biologic material by at least 0.1 micron, more preferably at least I micron, at all areas of the biologic material. To determine if a biologic material is coated, instruments capable of precisely measuring the contour height of thin films may be used. Such instruments include, for example, profilometers or interferometers. Preferably, a coating is sufficiently continuous that virtually no straight-line penetrable discontinuities or gaps are detectable in the coating overlying the biologic material, as detected using, for example, standard microscopy, phase-contrast microscopy or fluorescence microscopy. Preferably, such straight-line penetrable discontinuities or gaps should comprise less than 20%, and more preferably less than 5% of the surface area of the coating. It will be apparent that any number of discontinuities and gaps may exist in regions not overlying biologic material.

The term "complementary" refers to electronic topologic compatibility or matching together of interacting surfaces of a ligand molecule and its receptor, resulting in detectable binding using the appropriate assay technique. Thus, a receptor and its ligand can be described as complementary, as can the contact surface characteristics of a receptor and its ligand. Depending on the degree of complementarity of two ligands for a particular receptor as exhibited by their binding constants, one ligand may be said to more specifically bind relative to the other. Two nucleobase polymers are said to be "complementary" if the polymers are able to pair (as in Watson-Crick base-pairing) with corresponding bases in a given nucleic acid molecule of interest. The term "substantially complementary" indicates that at least about 80% of the nucleobases in a particular sequence are able to engage in base-pairing with corresponding bases of a nucleic acid molecule of interest. The term partially complementary: indicates that at least about 60% of the bases in a particular sequence are able to engage in base pairing with corresponding bases of a nucleic acid molecule of interest.

The term "contact" refers to physical contact. A biologic material is contacted with a detection reagent if there is no detectable separation between the biologic material and the reagent. A photoresist is contacted with a developer if a developer composition is contacted with the photoresist, or if irradiation is targeted to the photoresist, such that the photoresist is substantially removed in a specific region. Similarly, a biologic material is contacted with an ablation agent if the agent is contacted with the biologic material or if irradiation that effects ablation of a particular substance is targeted to the biologic material, such that ablation occurs.

A "detectable response" is any signal that may be detected in an assay, which may be performed with or without a detection reagent. Detectable responses include radioactive decay and energy (e.g., fluorescent, ultraviolet, infrared, visible) emission, absorption, polarization, fluorescence, phosphorescence, transmission, reflection or resonance transfer. Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition.

A "detection reagent" is any molecule that generates a detectable response indicative of the presence or absence of a substance of interest. Detection reagents include any of a variety of molecules, such as antibodies, nucleic acid sequences and enzymes. To facilitate detection, a detection reagent may comprise a marker.

A "developer" may be any treatment that dissolves an irradiated portion of a positive photoresist or an unirradiated portion of a negative photoresist, permitting selective removal of the dissolved regions. A developer may be a liquid or gas composition. Certain preferred developers comprise a non-aqueous mixture of solvents containing various ratios of ketone, amino, hydroxyl and amide moieties. Alternatively, a developer may be irradiation.

A "discrete region" is a localized area of a surface on which a biologic material is, was, or is intended to be attached. The region may have any convenient shape including circular, rectangular, elliptical, etc., and may be of any size, such as $100-10^6$ $\mu$um$^2$.

A "dye-sensitized polymer" is a polymer-dye composite, wherein the dye assists in absorbing radiant energy of a particular wavelength not significantly absorbed by the polymer, resulting in photoablation of the composite by concentrated laser irradiation. The dye may be a part of the composite as a noncovalent blend, or as a moiety covalently attached to the polymer.

The term "exposed" refers to a biologic material from which a photoresist layer has been substantially removed. Exposed biologic material is unprotected and is vulnerable to the action of, for example, a detection reagent or an ablative agent.

"Hybridization" refers to the base-pairing or aggregation of one nucleobase polymer to another nucleobase polymer via complementary regions. Such base-pairing or aggregation should be detectable using standard assays (e.g., detection of a marker linked to one nucleobase polymer). Whether or not a particular nucleobase polymer remains base-paired or aggregated with a target nucleobase polymer depends on the degree of complementarity, the length of the aggregated elements, and the stringency of the binding conditions. At a higher stringency, hybridization requires a higher degree of complementarity or length.

A biologic material is "immobilized" on a substrate if it is covalently or noncovalently attached to the substrate. Such attachment should be sufficient to result in substantially all (i.e., at least 50%, preferably at least 80% and more preferably at least 98%) of the material remaining attached to the substrate following exposure to the solvent of the photoresist and the developer (if any). Immobilization may be achieved using standard techniques for covalent and noncovalent attachment of a material to a substrate. Alternatively, immobilization may be achieved via specific receptor-ligand binding. In other words, a biologic material comprising a receptor may be immobilized on one or more ligands within a ligand array by contact with the array under conditions that permit specific receptor-ligand binding. Immobilization may be readily tested by separately contacting a test sample of the biologic material on a substrate with the photoresist solvent and its associated developer. If the biologic material remains attached to the substrate after contact with these solutions, then it is immobilized. In embodiments employing biologic material comprising tissue sections, cells, or viruses, determining if the biologic material remains attached may be accomplished using visual observation or microscopy. In embodiments employing biologic material smaller than that visualized by microscopy, other methods for determining adherence to the substrate surface may be used including, for example, fluorescence in situ hybridization, immunochemistry, scanning tunneling microscopy and surface acoustic wave methods.

"In situ methods" refer to the collection of methods available to those skilled in the art which produce position-composition relationships by forming a labeled ligand-receptor pair with a ligand or receptor in a biologic material immobilized on a solid phase. Thus, the labeled ligand or receptor co-localizes with the ligand or receptor it is designed to detect. These methods include, for example, histochemistry (i.e., the application of chemicals to react with specific chemical or enzyme compositions), immunocytochemistry (i.e., the application of antibodies to detect antigen compositions), fluorescence in situ hybridization (i.e., the application of labeled probes to detect nucleic acid compositions) and in situ PCR (i.e., the application of PCR to locally amplify a target sequence followed by hybridization with labeled probes). An "in situ assay mixture" is an assay mixture or mixtures contacting the surface of a biologic material in an "in situ method" which forms the labeled ligand-receptor pair. "Irradiation" refers to the application of radiation to a target. The amount of irradiation depends on the desired result of the irradiation. In general, irradiation is sufficient to achieve a desired chemical modification on an irradiated molecule. Within the methods described herein, a step of irradiating a photoresist is sufficient to result in substantial removal of irradiated positive resist, and prevent substantial removal of irradiated negative photoresist. Such a step may comprise contact of the photoresist with a developer and/or rinsing to effect substantial removal of irradiated positive photoresist or unirradiated negative photoresist. In general, irradiation of a positive photoresist layer is sufficient to permit substantial removal of photoresist from irradiated regions. Irradiation of a negative photoresist is sufficient to prevent substantial removal of photoresist from irradiated regions during exposure to developer and/or rinsing.

A "ligand," as used in this specification, is any molecule that is a candidate for specific binding by one or more receptor molecules of a type or types found in nature. It will be understood that many ligands will not specifically bind their intended receptor. For example, the majority of ligands in a drug analogue array will not be expected to bind their target receptor specifically. Further, the term "ligand" is not limited to molecules having any particular biological function. Ligands may be naturally-occurring or man-made molecules, and they can be employed in their unaltered state or as aggregates with other species. Ligands may be attached (covalently or non-covalently) to a substrate, either directly or via other molecules, such as linkers and/or spacers. Ligands may covalently or non-covalently modify a given receptor after binding the receptor. Such modifications include labeling, altering conformation, cleaving, covalently binding and intercalation. A ligand that is capable of modifying a target receptor in such a manner is said to comprise a "target receptor modifying group." Examples of ligands include, but are not restricted to, agonists and antagonists for cell membrane receptors, toxins and venoms, viral epitopes, hormones and hormone analogues, antibodies (polyclonal and monoclonal), cell membrane receptors, antisera reactive to specific antigenic determinants, enzymes, drugs, drug analogues, polynucleotides, nucleic acid, catalytic nucleic acids, peptides, catalytic peptides, peptide nucleic acids, nucleobase polymers, cofactors, lectins, sugars, polysaccharides, cells (naturally-occurring or genetically engineered), cellular membranes and organelles.

A "ligand-array" is a two dimensional matrix of ligands attached to a surface. "Ligand-receptor binding" refers to specific, detectable binding between a ligand and receptor through molecular recognition.

A "ligand-receptor pair" is a complex formed when a ligand and receptor bind through molecular recognition.

A "linker" is a molecule or group of molecules attached to a substrate and spacing a biologic material from the substrate. Linkers may further supply a labile linkage that allows a biologic material to be detached from the substrate. Labile linkages include photocleavable groups, acid-labile moieties, base-labile moieties and enzyme-cleavable groups.

A "marker" is an atom or molecule that permits the specific detection of a molecule comprising the marker in the presence of similar molecules without a marker. Markers include, for example radioactive isotopes, antigenic determinants, nucleic acids available for hybridization, chromophors, fluorophors, chemiluminescent molecules, electrochemically detectable molecules and molecules that provide for altered fluorescence-polarization or altered light-scattering.

A "mask" is a barrier that selectively permits the passage of irradiation to designated regions of a target photoresist. A mask may be a substantially transparent support material with substantially opaque regions in a precise pattern where it is desired that light be blocked when one side of the mask is illuminated. In some embodiments the substantially opaque regions are derived through a photographic process using a photoplotting device (e.g., as in masks commonly used in printed circuit board manufacturing). In other embodiments the mask is derived from a substantially transparent support material coated with a substantially opaque material which is photoablated by a narrowly focused laser producing precisely defined transparent regions (e.g., chrome on glass masks). The differential between the intensity of light transmitted by substantially transparent and substantially opaque regions as a percentage of the intensity of light transmitted by substantially transparent regions should be greater than 75%, more preferably greater than 90%, and most preferably greater than 99%. Importantly, the differential should be sufficient to permit irradiation of photoresist as defined above.

"Nucleic acid molecules" (or "nucleic acids") are polymers of nucleotides (i.e., compounds formed of phosphoric acid ($H_3PO_4$), a sugar, and a purine or pyrimidine base). Such polymers may be of any length, and include DNA and RNA molecules. Relatively short nucleic acid molecules (i.e., containing fewer than about 200 nucleotides) may be referred to as "oligonucleotides." Nucleic acid molecules are typically susceptible to degradation by nucleases.

A "nucleobase" is a nitrogenous heterocyclic group typically found in nucleic acids (such as the purine bases adenine and guanine, or the pyrimidine bases cytosine, thymine and uracil), or an analog of such a group. Analogs include, for example, purine bases in which the ring substituents are other than those found in adenine or guanine, or pyrimidine bases in which the ring substituents are other than those found in uracil, thymine and cytosine. A number of analogs of nucleobases are well known in the art; many of which have been tested as chemotherapeutic agents. Some of these are described herein; see also, e.g., *Beilstein's Handbuch der Organischen Chemie* (Springer Verlag, Berlin), and Chemical Abstracts, which provide references to publications describing the properties and preparation of such compounds.

A "nucleobase polymer" is a polymer of nucleobases linked to a backbone. The backbone may be naturally occurring (as in a nucleic acid molecule) or may be non-naturally-occurring. Nucleobase polymers with non-naturally-occurring backbones are preferably resistant to degradative enzymes. Representative examples include peptide nucleic acids (see Buchardt et al., PCT WO 92/20702 and Buchardt et al., U.S. Pat. No. 5,719,262), morpholino-based nucleobase polymers (see Summerton and Weller, U.S. Pat. No. 5,698,685; Summerton et al., U.S. Pat. No. 5,378,841 and Summerton and Weller, U.S. Pat. No. 5,185,444), peptide-base nucleic acid mimics or PENAMs (see Shah et al., U.S. Pat. No. 5,698,685), and polynucleosides with linkages comprising carbamate (see Stirchak and Summerton, *J. Org. Chem.* 52:4202, 1987), amide (see Lebreton et al., Synlett. February 1994:137), methylhydroxylamine (see Vasseur et al., J. Am. Chem. Soc. 114:4006, 1992), 3'-thioformacetal (see Jones et al., .J. Org. Chem. 58:2983, 1993), sulfamate (see Huie and Trainor, U.S. Pat. No. 5,470,967) and others (see Swaminathan et al., U.S. Pat. No. 5,817,781 and Freier and Altmann, *Nucl. Acids Res.* 25:4429, 1997, and references cited therein).

A "peptide nucleic acid" (PNA) is a molecule comprising repeating units of N-(2-aminoethyl)-glycine linked by amide bonds (see Buchardt et al., PCT WO 92/20702). Unlike the natural DNA backbone, no deoxyribose or phosphate groups are present. The bases are attached to the backbone by methylene carbonyl linkages.

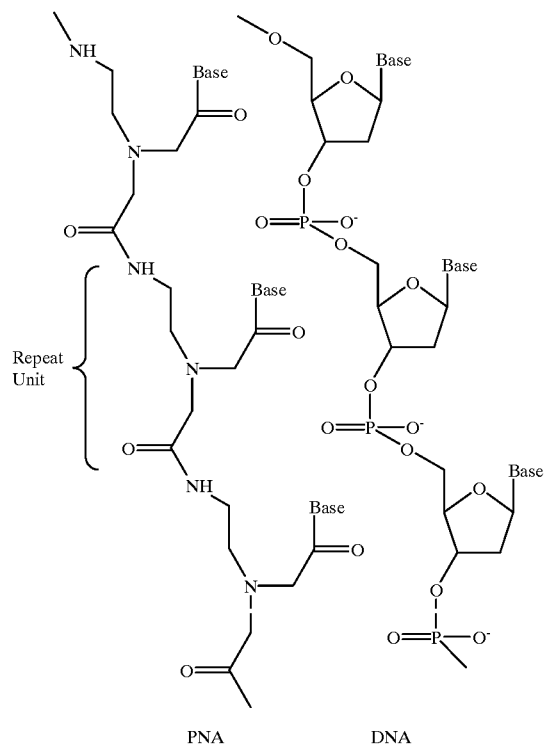

PNA            DNA

In specification, PNA sequences are written using the single-letter designation of the attached base just as DNA sequences are written. PNA sequences are distinguished from DNA sequences by an "NH$_2$" group at what would be the 5' end of a DNA sequence. For example, in this specification AGGTC-5' is a DNA sequence, while AGGTC-NH$_2$ is a PNA sequence. Certain preferred peptide nucleic acid polymers comprise a repeating unit of the form:

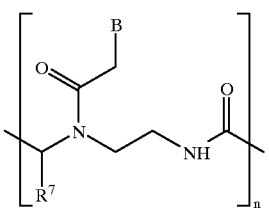

while each B is independently selected from the group consisting of nucleobases; each $R^7$ is independently selected from the group consisting of hydrogen, $C_1$–$C_8$ alkylamines and spacers; and each n is an independently selected integer ranging from 1 to 100.

A "peptide nucleic acid mimic" (PENAM) is a nucleobase polymer that comprises a repeating unit of the form:

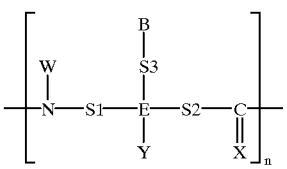

wherein each is E is independently selected from the group consisting of carbon and nitrogen; each W is independently selected from the group consisting of hydrogen and spacers; each Y is independently selected from the group consisting of hydrogen and spacers, in repeating units wherein E is carbon; each Y is a lone pair of electrons, in repeating units wherein E is nitrogen; each S1 is optional, and if present is an independently selected first spacer; each S2 is optional, and if present is an independently selected second spacer; each S3 is optional, and if present is an independently selected third spacer; each X is independently selected from the group consisting of oxygen and sulfur; each B is independently selected from the group consisting of nucleobases; N is nitrogen; and each n is an independently selected integer ranging from 1 to 100.

A "photocleavable group" is a portion of a molecule that is cleaved upon exposure to light of a particular wavelength and intensity.

The term "photoresist" refers to a material that, upon irradiation, sustains a chemical reaction that allows irradiated and non-irradiated regions to be separated from one another. Although the separation may be simultaneous with irradiation (e.g., in laser ablation), it often requires an additional process step or steps (e.g., exposure to a developer). The chemical reaction may involve the formation or breakage of chemical bonds with such bond changes occurring in either an intramolecular or intermolecular fashion. In most applications, a photoresist is applied to a flat surface as a relatively thin liquid layer and evaporated. A "negative photoresist" refers to a photoresist that leaves photoresist on the surface in irradiated regions, while a "positive photoresist" refers to a photoresist that leaves photoresist on the surface in regions that were not irradiated. Unirradiated photoresist is not covalently attached to the substrate. Photoresists suitable for use within the methods provided herein generally satisfy the following criteria:

(1) the photoresist provides a coating on the biologic material that maintains integrity during the assay(s) of interest, thereby preventing contact of reagents with biologic material in regions covered by the photoresist layer;

(2) irradiation of the photoresist results in differential solubility of the photoresist in irradiated regions, relative to non-irradiated regions;

(3) for positive photoresists (or negative photoresists in methods involving ablation), irradiation can be performed with light of a wavelength that does not substantially react with (or photodegrade) the biologic material;

(4) the photoresist solvent (and developer, if needed) does not adversely affect the ability to perform an assay of interest using the exposed biologic material;

(5) for positive photoresists (or negative photoresists in methods involving ablation), the photochemical reaction undergone by the photoresist is substantially inert with respect to biologic material in contact with the photoresist. In other words, such photoresists have photoreactive molecules that effect a change in the solubility profile of the photoinactive polymer while not adversely affecting the underlying biologic material;

(6) for assays in which biologic material is ablated, the stripper should not adversely affect the ability to perform an assay of interest using the exposed biologic material.

A "polymer" is a molecule formed by the covalent linkage of monomeric subunits. Photoresists typically contain polymers, such as the polymers described in greater detail below. Polymers include dye-sensitized polymers.

A "primer" is a nucleic acid or other nucleobase polymer designed to be sufficiently complementary to a target sequence in a denatured nucleic acid (in relation to its length) to be bound under selected stringency conditions so as to serve as a ligand for a polymerase. A primer should bind sufficiently to permit detection of the target sequence in a PCR assay.

A "probe" is a nucleic acid or other nucleobase polymer designed to be sufficiently complementary to a target sequence (in relation to its length) to be bound detectably under selected stringency conditions. A probe is typically labeled with a marker, such as a fluorescent moiety.

"Radiation" refers to energy which may be selectively applied, including energy having a wavelength of between $10^{-14}$ and $10^4$ meters. Radiation includes electrons, x-rays and particles from radioisotopic decay, as well as light (e.g., visible, ultraviolet or infrared).

A "receptor" is a molecule that specifically binds a given ligand. Receptors, as used herein, are generally naturally-occurring molecules, and can be employed in their unaltered state or as aggregates with other species. Examples of receptors include, but are not limited to, antibodies, cell membrane receptors, monoclonal antibodies, antisera reactive to specific antigenic determinants, enzymes, drugs, polynucleotides, nucleic acids, peptides, cofactors, lectins, sugars, polysaccharides, cells, cellular membranes and organelles.

A "separate region" of biological material or photoresist is a region that does not overlap or contact other separate regions. In other words, a photoresist coating from which photoresist has been removed from 100 separate regions will expose underlying biologic material in 100 distinct, non-overlapping regions.

"Stripping" refers to the substantial removal of photoresist by strippers. Strippers are liquid chemical media used to remove photoresists after processing is finished. The exact composition depends on the composition of the photoresist.

A "substance of interest" is a compound, cell or virus that may be present within a biologic material. Analysis of a region of a biologic material for the presence or absence of a substance of interest includes qualitative and quantitative assays designed to detect a specific substance, or may be assays designed to determined the identity of an unknown substance. Suitable assays include electrophoresis, chromatography, mass spectrometry, DNA sequencing, nucleic acid hybridization, PCR and peptide sequencing, as well as assays to detect antibody binding or enzyme reactivity.

The phrase "substantially react" refers to effecting a substantial molecular change. Within the methods described herein, a light does not "substantially react" with a photoresist if it is insufficient to result in substantial removal of irradiated positive photoresist, or insufficient to prevent substantial removal of irradiated negative photoresist. Whether a light "substantially reacts" with a photoresist depends on the wavelength, duration and intensity of the light, as well as the nature of the photoresist. In some embodiments, a light that does not "substantially react" with a photoresist may still result in detectable changes in a photoresist. For example, such a light may result in the removal of several tens of nanometers of the surface of a positive photoresist, which would be detectable by sensitive methods such as interferometry. Alternatively, such a light may result in a small number of cross-linking reactions in a fraction of the polymeric component of a negative photoresist, which would be detectable by sensitive methods such as get permeation chromatography. The differential between the changes induced in a photoresist by lights that do and do not "substantially react" as a percentage of changes induced by a light that does "substantially react" should be greater than 75%, more preferably greater than 90%, and most preferably greater than 99.9%. Importantly, the differential should be sufficient to permit irradiation of photoresist as defined (see "irradiation" above). Similarly, a process or reagent does not "substantially react" with a biologic material if contact with such process or reagent does not result in a substantial change to a detectable response from either an assay or a detection reagent that would otherwise occur in the absence of such a process or reagent (e.g., see definition of "ablation" above for examples of agents that result in substantial changes to detectable responses). As discussed with light above, a process or reagent that does not "substantially react" with a biologic material may in some embodiments still result in detectable changes in the biologic material. Such changes could include, for example, covalent modification of the material, or in a modification of a physical property (e.g., antigenicity, reactivity, adhesion properties of cells, integrity of membranes or cellular organelles, and enzymatic activity). The important characteristic of a process or reagent that does not "substantially react" with a biologic material, however, is that a desired detectable response from the biologic material is substantially similar in the presence or absence of the process or reagent. In preferred embodiments, the detectable response is not altered by more than 50%, 25%, and most preferably 5%.

Photoresist is said to be "substantially removed" from an underlying biologic material the biologic material no longer contains a "coating," as described above. In other words, any residual photoresist should not prevent contact with an ablative agent or detection reagent, such that a signal obtained from a substance of interest in a biologic material from which photoresist has been removed is within 50% (preferably within 25%, more preferably within 5%) of the signal obtained from the biological material that has never been covered with photoresist. Preferably, the contour height at all points over the biologic material should be substantially the same as (i.e., within 0.1 microns of) the contour height of the biologic material alone. To determine if given conditions result in substantial removal of photoresist, instruments capable of precisely measuring the contour height of thin films may be used, such as, for example, a profilometer or interferometer. Alternatively, or in addition, test assays may be performed on a given biological material before and after photoresist application and removal. In embodiments employing positive photoresists comprising diazoquinones, fluorescence microscopy may also be used to assess whether residual photoresist remains over a biologic material. Residual photoresist comprising diazoquinone exhibits a red fluorescence, which should be undetectable by fluorescence microscopy following substantial removal of photoresist.

A "substrate," as used herein, is any solid surface on which a biologic material is immobilized.

"$T_M$" refers to the temperature at which two complementary strands of nucleobase polymers (e.g., DNA:DNA, PNA:DNA or PNA:PNA) dissociate into individual nucleobase components. An approximate value of $T_M$ for a DNA duplex in degrees centigrade is given by the formula:

$$T=16.6 \log|M|+0.41|P_{gc}|+81.5-P_m-B/L$$

where M is the molar concentration of $Na^+$ to a maximum of 0.5, $P_{gc}$ is the percent of G or C bases in the oligonucleotide between 30% and 70%, $P_m$ is the percent mismatch, B is 675 for oligonucleotides less than 100 bases, and L is the probe length in bases. For a PNA:DNA heteroduplex in 100 mM NaCl, the $T_m$ is approximately 1° C. higher per base pair than the corresponding DNA duplex.

REGIONAL ANALYSIS OF BIOLOGIC MATERIAL

The present invention provides methods for the analysis of discrete regions of a biologic material. Such regions may be of essentially any size or shape, and the biologic material may, but need not, be arranged in an array.

A Substrate Selection

Essentially any conceivable substrate may be used within the methods provided herein, including biological, nonbiological, organic and inorganic substrates, as well as substrates that are a combination of any of these. The substrate may have any convenient shape, such as a disc, square, sphere, circle, or any other suitable shape, and may be formed, for example, as a particle, strand, precipitate, gel, sheet, tubing. sphere, container, capillary, pad, slice, film, plate or slide. The substrate preferably forms a rigid support on which to support the biologic material, and is preferably flat, although it may take on a variety of alternative surface configurations, including having raised and/or depressed regions. The substrate may be prepared from essentially any material. For instance, a substrate may comprise functionalized glass, Si, Ge, GaAs, GaP, $SiO_2$, $SIN_4$, modified silicon, photoresist, biolayers, silane layers or any one of a wide variety of polymers such as polytetrafluoroethylene, polyvinylidenedifluoride, polystyrene, polycarbonate, polyethylene, polypropylene, nylon or combinations thereof. Other substrate materials will be readily apparent to those of skill in the art. In a preferred embodiment the substrate is flat glass.

The surface of a substrate may, but need not, be composed of the same material as the substrate. Surface materials include, but are not limited to, polymers, plastics, resins, polysaccharides, silica or silica-based materials, carbon, metals, inorganic glasses, membranes or any of the above-listed substrate materials. Preferably, the surface contains reactive groups, such as carboxyl, amino and/or hydroxyl groups. Most preferably, the surface will be optically transparent and will have surface Si-OH functionalities, such as are found on silica surfaces. Surfaces are also preferably rigid.

B. Attachment of Linkers

Within certain embodiments, one or more linkers may be attached to a substrate surface, using any suitable technique. Linkers are optional molecules that may link a biologic material to the surface. A linker may serve a variety of functions, including spacing the biologic material from the surface, spacing the biologic molecules from one another, facilitating receptor recognition of immobilized ligands, or supplying a labile linkage that allows biologic material to be detached from the surface. According to preferred embodiments, linkers may be selected based on their hydrophilicity, hydrophobicity or charge properties so as to promote adhesion of the biologic material (see Cozzette, U.S. Pat. Nos 5,200,051 and 5,466,575).

Within certain embodiments, a linker will space biologic molecules from one another on the substrate surface so that less than 20% of the molecules contact one another (i.e., at least 80% of the linkers are separated from other linkers by a distance greater than the diameter of the biologic molecule). Such spacing is beneficial to facilitate recognition of the biologic molecules by other molecules such as receptors, and those found in ablative agents, detection reagents, and assays. Proper linker spacing may be achieved using methods familiar to those of skill in the art. For example, the surface spacing or density of a linker that covalently attaches to the substrate surface may be modified by varying the linker concentration and duration of contact between the substrate surface and a linker solution. The final density of the linker on the surface may be monitored by numerous methods familiar to those skilled in the art. For example, the density on silica surfaces may be monitored by measuring the decrease in surface isolated free silanols using either diffuse relectance infrared Fourier transform spectroscopy (i.e., DRIFTS) or 29Si NMR spectroscopy as described by Daniels et al., *Mat. Res. Soc. Symp. Proc.* 435:215, 1996. Other methods for measuring the linker density will be apparent to those skilled in the art. The choice of linker density will be a function of the size of the biologic molecule. In preferred embodiments, the linker density per square micrometer will be less than 10000, 2500, 1000, 400, and 100 for biologic molecules with a diameter less than 100, 200, 300, 500 and 1000 angstroms, respectively. In particular, a typical protein molecule with a diameter less than 500 angstroms will be linked to a surface with a density of linkers per square micrometer of less than 400. The effective diameter of biologic molecules is readily determined by methods familiar to those of skill in the art including gel permeation chromatography, atomic force microscopy, and light scattering.

Preferably, at least one linker (at least 5 atoms long, preferably 6–50 atoms long) is used, to permit interaction and promote adhesion of biologic material. Linkers may comprise, for example, aryl containing molecules, ethylene glycol oligomers containing 2–10 monomer units, diamines, diacids, amino acids, silane layers, or any of a wide variety of polymers such as polytetrafluoroethylene, polyvinylidenedifluoride, polystyrene, polycarbonate, polyethylene, polypropylene, nylon, polyvinyl alcohol, polyacrylamide, or combinations thereof. Other linker materials will be readily apparent to those of skill in the art.

The linker molecules may be, for example, silane reagents, especially those of the formula $R'_n Si(OR)_{4-n}$ where n is an integer that may be 0, 1 or 2, and R' is typically an aliphatic group comprising 3–12 carbon atoms with a terminal amine functionality, and R is a lower alkyl group comprising 1–4 carbon atoms or a hydrogen radical (see Weetall, *Methods in Enzymology* 44:134, 1976). The silane reagent is usually mixed with a suitable water containing solvent to form a liquid mixture that is applied to the substrate surface by any number of ways including, but not limited to, spin-coating, dip-coating, spray-coating and microdispensing. Photolithographic techniques such as "lift-off" or using a photoresist cap may be used to pattern the linker molecules. The liquid film is then heated to a temperature of about 90–250° C. for a period of time effective to establish a covalent addition to the surface. Typically about 5 to 30 minutes of heating at this temperature is required. Other functionalities for the R' aliphatic group are available besides amino including bromo, chloro, carboxy, diamino, hydroxy, dihydroxy, phenyl, mercapto and isocyanato. In alternative embodiments, the linker molecules are adsorbed to the surface of the substrate instead of being covalently attached. For example, (poly)lysine and gelatin may be adsorbed to the surface to facilitate adhesion of biologic material. Most preferably, however, the surface will be covalently derivatized with aminopropyltrimethoxysilane (Gelest, Inc., Tullytown, Pa.).

In a preferred embodiment, linkers are organoalkoxysilanes containing one or more reactive groups. Reactive groups include, for example, amino, hydroxy, epoxy, carboxyl, sulfhydryl or halogen groups. Reactive groups are preferably on the distal or terminal end of the linker molecule opposite the surface. In preferred embodiments, the organoalkoxysilanes are 3-aminopropyltriethoxysilane (i.e., APES), bearing an amino group, and/or bis(2-hydroxyethyl)-3-aminopropyltriethoxysilane (i.e., HAPES), bearing two hydroxyl groups.

Alternatively, or in addition, a linker may be selected to permit removal of immobilized biologic material. Such a linker may be, for example, photocleavable, acid labile, base-labile or cleavable by an enzyme. The use of a photocleavable linker permits removal of biologic material by irradiation with light at a wavelength that may be chosen to be distinct from wavelengths used to perform other process steps. An acid- or base-labile linker comprises a labile moiety that permits the removal of ligand upon exposure to acid or base. An acid or base may be, for example, vapor-phase trifluoroacetic acid (TFA) or $NH_3$, respectively. Acid-, base-, and photo-labile linker molecules are known in the art, and are commercially available (see *The Combinatorial Chemistry Catalog*, Nova Biochem, Inc., 1998). One suitable acid labile linker has the formula:

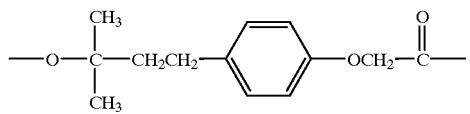

The use of such linkers may be particularly beneficial in receptor-ligand binding screens, as described in greater detail below. Both photocleavage and vapor-phase cleavage of ligand-arrays allow separated ligands to remain co-localized with their site of attachment and/or synthesis. Ligand separation from the support is essential for the formation of many ligand-receptor pairs. Co-localization is particularly advantageous when an in situ assay is used to determine ligand-receptor binding. In such an assay, determining the location of binding also determines the identity or reagent history of the bound ligand. It is particularly preferable to screen arrays of drug candidates using in situ assays.

A linker may also, or alternatively, comprise a recognition sequence for cleavage by an enzyme. Such a sequence enables removal of biologic material by contact with the enzyme. An enzyme-cleavable group may be chosen so as to be substantially cleavable with a protease, non-specific nuclease, specific nuclease or enzyme secreted by a cell. Preferably, the enzyme-cleavable moiety connects the linker with the biologic material so as to enable the removal of biologic material upon contact with a living cell. Most preferably, the cell will secrete an enzyme that detaches the biologic material, which subsequently diffuses into the cell and affects some internal biologic process. For example, nucleobase polymers attached via protease-sensitive linkages may be used to conduct antisense experiments on cells growing in direct contact with the surface of the array. Biologic material separation from the support is essential for transmigration of the ligand through the cell membrane. Cell-induced cleavage of the nucleobase polymer also allows the separated ligands to remain co-localized with their site of attachment. Co-localization is particularly advantageous when a phenotypic cellular assay is used to determine modulation of gene expression by the nucleobase polymer. In such an assay, determining the location of the phenotypic change determines the sequence of the nucleobase polymer affecting the change, as well as the base sequence of its intracellular target.

A linker may be covalently attached or adsorbed to the surface (via C—C, C—N, C—O, C—S, Si— or other chemical bonds) according to methods well known in the art (see *Methods in Enzymology*, vol. XLIV, edited by Klaus Mosbach, (1976), Academic Press N.Y.). For example, linkers with hydroxy groups may be attached to a surface with a 2% solution of HAPES in 95:5 ethanol:$H_2O$ for 10 minutes, followed by rinsing, with ethanol and curing at 120° C. for 15 minutes. Linkers with amino groups are attached similarly except that APES is substituted for HAPES. Organoalkoxysilanes may generally be attached to a surface via siloxane bonds.

C. Immobilization of Biologic Material

As noted above, any of a variety of biologic materials may be immobilized on a substrate (with or without the use of linkers). Such biologic materials include, but are not limited to, contiguous and non-contiguous biologic material that is living, dead, fixed, not fixed, intact, disaggregated, in solution, desiccated, grown on a substrate or grown in solution. This includes any tissue, tissues, eukaryotic cell, bacteria, virus or cell components including, for example, organelles, membranes, chromosomes, nucleic acids, peptides, proteins, enzymes, cofactors, lectins, sugars or polysaccharides. Although the invention herein is primarily described with regard to fixed, deparaffinized and stained tissue sections or air-dried, stained cells, it is readily apparent to those skilled in the art that the invention could be applied to other forms of biologic material.

Also included within the definition of "biologic material" is nucleobase polymers that mimic nucleic acid, including nucleobase polymers with a non-naturally occurring backbone (e.g., PNA, PENAM and other such polymers). As noted above, there are many nucleobases that may be incorporated into a nucleobase polymer, Such nucleobases include, for example, purine bases and pyrimidine bases, which may be naturally-occurring or analogs of naturally-occurring bases. A large variety of analogs have been described that exhibit properties that may be advantageous in particular array applications. For example, in some cases, it may be desirable to incorporate a nucleobase that binds non-specifically at a particular position. The nucleobase present in inosine is an example of such a non-specific analog. This can be used to incorporate degeneracy into nucleobase polymers at particular positions which might be particularly useful, for example, in targeting a closely related family of target nucleic acids that are homologous except for one or a few positions in their nucleobase sequences. Inosine can pair with all four natural nucleobases, although the strength of binding varies: dC>dA>dG/T. Alternatively, the universal nucleobase 3-nitropyrrole-2'deoxynucleoside may be used to introduce degeneracy. In this strategy, the analog does not hybridize significantly to the other four natural nucleobases and makes up some of the duplex destabilization by acting as an intercalating agent.

Other types of modified nucleobases that may be of particular interest are those which enhance binding, affinity. For example, diaminopurine can form three hydrogen bonds with thymine, whereas adenine and thymine form only two. Similarly, pyridopyrimidine nucleobases can be used in place of cytosine to provide stronger pairing with guanine.

Nucleobases can also comprise any of a variety of "target receptor modifying groups". By way of illustration, nucleobases can function as cross-linking moieties. For example, 6-bromo-5,5-dimethoxyhexanohydrazide can be introduced into the $C^4$ position of cytidine to alkylate and thereby crosslink guanosine (see Summerton and Bartlett, *J. Mol. Biol.* 122:145, 1978). $N^4$, $N^4$-Ethano-5-methylcytosine can be used to similar effect (see Webb and Matteucci, *J. Am. Chem. Soc.* 108:2764, 1986 and Cowart et al., *Biochemistry* 28:1975, 1989).

A wide range of purine and pyrimidine analogus exhibiting various properties is known in the art (reviewed in Conholly, *Methods Enzymol.* 211 :36, 1992; Lin and Brown, *Methods Mol. Biol.* 26:187, 1994 and Meyer, *Methods Mol. Biol.* 26:73, 1994). An exemplary but not exhaustive list of such analogs includes: 1-methyladenine, 1-methylguanine, 1-methylinosine, 1-methylpseudouracil, 2-methylthio-$N^6$-isopentenyladenine, 2-thiocytosine, 2-methyladenine, 2-methylguanine, 2-thiouracil, 2,2-dimethylguanine, 2,6-diaminopurine-3-methylcytosine, 3-(3-amino-3-N-2-carboxypropyl)-uracil-4-acetylcytosine, 4-thiouracil, 5-fluorouracil, 5-iodouracil, 5-bromouracil, 5-methyluracil, 5-methyl-2-thiouracil, 5-methoxyaminomethyl-2-thiouracil, 5-chlorouracil, 5-carboxymethylaminomethyl-2-thiouracil, 5-methylaminomethyluracil, 5-carboxyhydroxylmethyluracil, 5-carboxymethylaminomethyluracil, 5-methoxyuracil, 5-methylcytosine, 7-metlhylguanine, 7-deazaguanine, 7-deazaadenine, β-D-mannoseylqueosine, β-D-galactosylqueosine, dihydrouracil, hypoxanthine, inosine, N-uracil-5-oxyacetic acid methylester, $N^6$-methyladenine, $N^6$-isopentenyladenine, pseudouracil, queosine, uracil-5-oxyacetic acid methylester, uracil-5-oxyacetic acid and xanthine.

The biologic material may be immobilized on the substrate by numerous methods including, but not limited to, centrifugation, spraying, dip-coating, microdispensing or photolithography. Alternatively, any of the aforementioned may be synthetically established on the surface by any number of methods familiar to those skilled in the art, including but not limited to, solid-phase nucleic acid synthesis (e.g., phosphoramidite or H-phosphonate methods), solid-phase peptide synthesis (e.g., the "Merrifield Method," see Merrifield, *J. Am. Chem. Soc.* 85:2149, 1963), PCR, in vitro RNA synthesis using an RNA polymerase, protein synthesis using an in vitro protein translation system (e.g., reticulocyte lysate systems), and photolithographic methods for synthesizing peptides, nucleic acids and other biologically relevant polymers on a substrate (see U.S. Pat. Nos. Brennan, 5,474,796; Pirrung et al., U.S. Pat. No. 5,143,854; McGall et al., U.S. Pat. No. 5,412,087; Fodor et al., U.S. Pat. No. 5,445,934 and Fodor et al., 5,510,270).

In certain embodiments, the biologic material is provided with stains, although it will be understood that stains are not required elements of the invention. Stains may be selected based upon their ability to facilitate localization or visualization of the biologic material. Such stains are well known to those in the art and include, for example, hematoxylin, eosin, Masson's trichrome, methylene blue, colloidal iron, periodic acid Schiff (PAS) and combinations of these. In alternative embodiments, the biologic material may be visualized using an in situ ligand-receptor pair formed between an endogenous receptor and exogenously added ligand, or an endogenous ligand and exogenously added receptor. The pair may produce, for example, a differential color, absorption of electromagnetic radiation, optical interference, electric conduction, radioactive decay, fluorescence, chemiluminescence, phosphorescence, or a molecular shape detectable by scanning tunneling microscopy (STM) or atomic force microscopy (AFM), either by itself or via other covalently and non-covalently linked molecules, labels, nuclear isotopes, antibodies, or enzymes so as to facilitate localization or visualization of the biologic material. The application of stains, ligands, or receptors may be applied to the biologic material prior to, or after it is brought in contact with the substrate surface. According to other embodiments, the biologic material may be located or visualized without stains, ligands, or receptors using, for example, phase-contrast or dark-field microscopy. Other methods of locating and visualizing the biologic material will be apparent to those skilled in the art. Most preferably, however, the stains will be hematoxylin and eosin applied after the biologic material is contacted with the substrate surface.

Within certain embodiments, a biologic material may be immobilized via a specific binding to a separate immobilized molecule (e.g., a receptor-ligand interaction). For example, a biologic material may be applied to the surface of a ligand array, which comprises multiple distinct ligands in known discrete regions. Biologic material that is not specifically bound may then be removed, leaving any specifically bound biologic material. Such biologic material is considered imniobilized. It will be apparent that biologic material may be immobilized over only a small portion of the li,and array, if at all. Nonetheless, a ligand array that is contacted with a biologic material under conditions that facilitate a receptor-ligand interaction of interest is considered to be immobilized biologic material, within the context of the present invention.

D. Application of Photoresist

Following immobilization, the biologic material is coated by photoresist. Any suitable photoresist may be used for this purpose, provided that the following criteria are satisfied:

(1) The photoresist provides a coating on the biologic material that maintains integrity during the assay(s) of interest, thereby preventing contact of reagents (e.g., ablative agents or detection reagents) with biologic material in regions covered by the photoresist layer. Photoresists most likely to display this property may be identified by considering the solubility profile of the photoinactive component, as described herein. This property may be readily identified by contacting photopatterned films of candidate photoresists with desired reagents and assaying for evidence of film instability such as dissolution, hazing, cracking and dehiscence.

(2) Irradiation of the photoresist results in differential solubility of the photoresist in irradiated regions, relative to non-irradiated regions.

(3) For positive photoresists (or negative photoresists in methods involving ablation), such irradiation can be performed with light of a wavelength that does not substantially react with (or photodegrade) the biologic material.

(4) The photoresist solvent (and developer, if needed) does not adversely affect the ability to perform an assay of interest using the exposed biologic material. This property may be readily confirmed by contacting a test sample of biologic material with the photoresist solvent and developer, and determining if the desired assay yields a result that is similar to that obtained with a control sample of biologic material (i.e., a signal that is not altered by more than 50%, preferably 25% and most preferably 5%). As a practical matter, the majority of photoresist solvents are chemically inert organic solvents that would not be expected to chemically modify biologic material, although they may result in changes to secondary, tertiary, and quaternary structures. Developers are typically organic solvents for negative photoresists, and aqueous bases for positive photoresists. Again, as a practical matter, it will be readily apparent to one skilled in the art whether a particular biologic material is compatible with a particular developer. For example, the use of an aqueous base would be expected a priori to be incompatible with the isolation of RNA (base labile), but compatible with the isolation of DNA (base stable).

(5) For positive photoresists (or negative photoresists in methods involving ablation), the photochemical reaction undergone by the photoresist is substantially inert with respect to biologic material in contact with the photoresist. In other words, such photoresists have photoreactive molecules that effect a change in the solubility profile of the photoinactive polymer while not adversely affecting the underlying biologic material. Photoactive components with these properties may be selected by identifying those photoreactive molecules that undergo substantially intramolecular photoreactions, or photoreactions that are highly specific for a class of molecules not attached to the substrate. The photoactive component will be further selected based on the wavelength of light necessary to affect a substantial photoreaction. Preferably, the photoactive component will react to radiation in the ultraviolet (UV) or visible portion of the electromagnetic spectrum. More preferably, the photoactive component will be reactive to radiation in the near UV or visible portion of the spectrum having a reactivity to light with a wavelength greater than about 250 nm, 300 nm, 350 nm and 400 nm.

(6) For assays in which biologic material is ablated, the stripper should not adversely affect the ability to perform an assay of interest using the exposed biologic material. This property may be assessed as described above for solvents and developers.

It will be apparent that there are many different photoresist compositions that are suitable for use within the methods provided herein. Based on the teachings of the present specification, those of ordinary skill in the art will be readily able to optimize a photoresist system for a particular application using only routine analyses.

Within certain embodiments, the positive photoresist is from the class of commercially available diazoquinone containing positive photoresists (see U.S. Patent Nos. Steinhoff et al., 3,402,044; Moore, U.S. Pat. No. 2,797,213; Endermann et al., U.S. Pat. No. 3,148,983; Schmidt, U.S. Pat. No. 3,046,118; Neugebauer et al., U.S. Pat. No. 3,201,239; Sus, U.S. Pat. No. 3,046,120; Fritz et al., U.S. Pat. No. 3,184,310; Borden, U.S. Pat. No. 3,567,453; and Pampaione, U.S. Pat. No. 4,550,069). Positive photoresists containing diazoquinone provide that irradiated regions can be solubilized with dilute, aqueous, alkaline solutions while non-irradiated regions are substantially insoluble in dilute, aqueous, alkaline solutions. Non-irradiated regions as well as irradiated regions, however, are rapidly solubilized by a wide variety of organic solvents well known to those in the art. Stripping of positive photoresist is preferably performed by immersion in acetone.

Other suitable photoresists are as described in co-pending application entitled "Solvent-Resistant Photosensitive Compositions." Such a photoresist generally comprises a polyamide derivative formed by the condensation of (1) a diamine mixture comprising a N-alkyl-2-nitro diamine and at least one of 1,4-phenylenediamine or 1,3-phenylenediamine and (2) a diacid chloride mixture comprising isophthaloyl chloride. Preferred N-alkyl-2-nitro diamines include $N^1$-methyl-2-nitro-p-phenylenediamine and 3,3'-dinitro-4,4'-di-N-methylaminodiphenyl ether. Preferred mole ratios of the diacid mixture to the diamine mixture range from 0.980 to 1.020.

One such photoresist comprises a polyamide derivative having a repeating unit represented by the following general formula:

where Z is 20 to 50 mole percent, and more preferably 20 to 35 mole percent, a structure comprising:

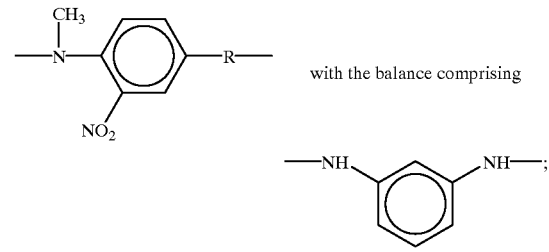

and Y is 10 to 100 mole percent a structure comprising:

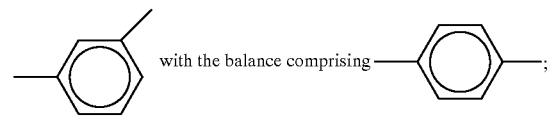

and R is a divalent organic group without particular restrictions. In some embodiments R may be selected from the group consisting of:

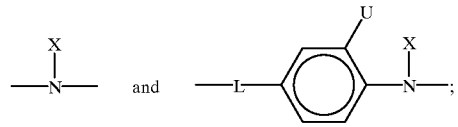

where X is H or $CH_3$; L is direct link, O, $CH_2$, $N(CH_3)$, $C(CH_3)_2$, $C(CF_3)_2$, $SO_2$, CO, CONH, $O(C_6H_4)_2$, S, $C(C_6H_5)_2$ or $C(CF_3)(C_6H_5)$; and U is H, $NO_2$ or $CH_3$. In preferred embodiments R is NH.

In a second embodiment, the photoresist comprises a polyamide derivative having a repeating unit represented by the following, general formula:

(2)

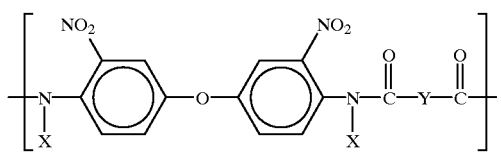

where X is 10 to 100 mole percent CH₃ with the balance H; and Y is 0 to 50 mole percent a structure comprising:

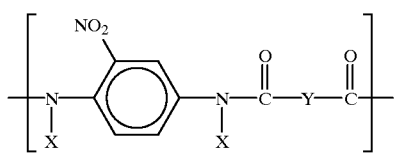

Within a third embodiment, the photoresist comprises a polyamide derivative having a repeating unit represented by the following general formula:

(3)

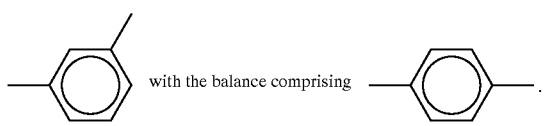

where X is 10 to 50 mole percent CH₃, and more preferably 10 to 20 mole percent CH₃, with the balance H; and Y is 20 to 100 mole percent a structure comprising:

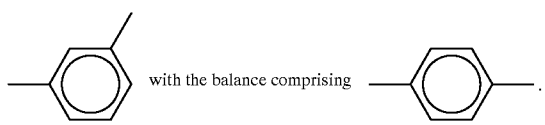

The above polyamide compositions provide dry films that are resistant to numerous solvents. Irradiation of these films with 365 nm light results in intramolecular photo-oxidation as follows:

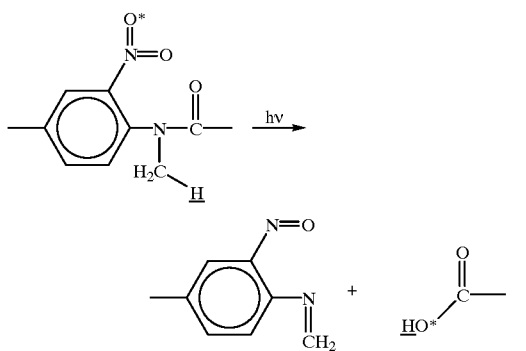

This reaction is known to be substantially intramolecular (for a review, See Pillai, *Synthesis* p. 1, 1980). As such, irradiation does not result in side-reactions with biologic material in contact with the film. Irradiated regions may be selectively solubilized by non-aqueous developers. Without wishing to be bound by any particular theory, the photopatterning mechanism is believed to be a consequence of both polymer chain cleavage, and the appearance of acidic carboxyl groups.

Diazoquinone-containing positive photoresists generally comprise a non-photoactive phenol-formaldehyde resin in concentration from about 10 to 40 wt % and a photosensitive diazoquinone in concentration from about 10 to 40 wt % in an organic solvent, such as 2-ethoxyethyl acetate or 1-methoxy-2-propyl acetate. Other additives, such as surfactants, may be present in minority fractions to promote planarization of the photoresist. The photolytic response of these photoresists reflect the photochemistry of the photosensitive diazoquinone often also referred to as a diazoketone, diazo-oxide, diazoanhydride, or quinone diazide, a chemical of the general form:

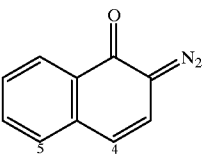

where the most commonly used versions of the general form are substituted at positions 4 or 5 with an —SO₂R group, where R consists of a very large variety of functionalities including sulfonic acid esters and amides of both monomeric and polymeric hydroxy, phenoxy, and amino compounds well described in the patent literature and familiar to those skilled in the art (described extensively in DeForest, *Photoresist Materials and Processes*, McGraw-Hill, 1975). Importantly, the primary photochemical behavior of the diazoquinone is substantially the same regardless of the composition of R.

Although the mechanism is not completely understood, and not wishing to be bound by any particular theory, absorption of any radiation with wavelengths from about 220 to 450 nm at ambient conditions is thought to raise the diazoquinone (1) to a higher energy state (see Pacansky and Lyerta, *IBM J. Res. & Dev.* 23(1):42, 1979). This higher energy state decomposes very rapidly with loss of nitrogen gas from the diazo group to form an unstable and very reactive keto-carbene (II) as shown:

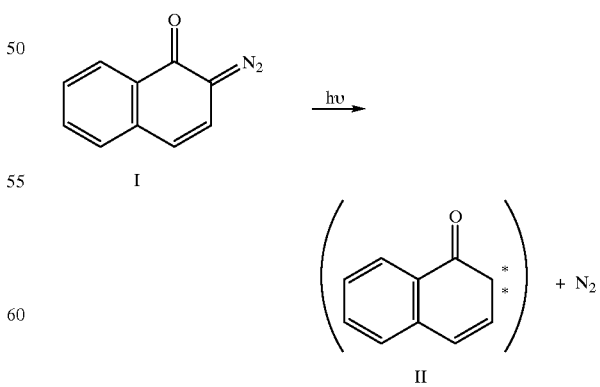

The transient species immediately isomerizes by ring contraction to a more stable intermediate called a ketene (111) as shown:

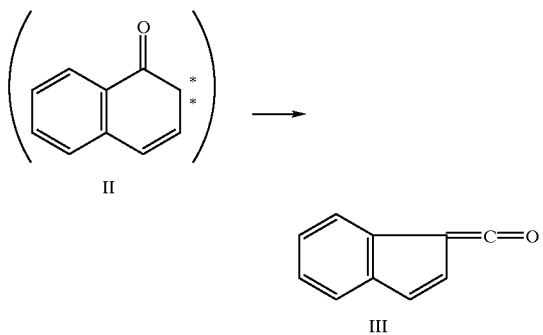

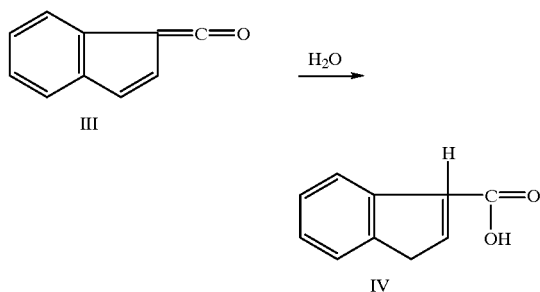

The ketenes themselves are quite reactive and combine readily with many reagents. It is thought that the ketenes combine with trace water to form the indene carboxylic acid (IV) as below:

It is thought that this sequence of events which includes the photolytic conversion of an initially insoluble diazoquinone (I) to an acid species (IV) soluble in aqueous alkaline solutions leads to a differential solubility in alkali between irradiated and non-irradiated photoresist.

It will be readily apparent to those skilled in the art that the photoresist may also be selected from a wide variety of negative photoresists. In contrast to positive photoresists, negative photoresists typically achieve differential solubility through an intermolecular cross-linking reaction in irradiated areas. Irradiated areas then become insoluble in all solvents. Numerous negative photoresists have been described in the patent literature, and are familiar to those skilled in the art (described extensively in DeForest, *Pholoresist Materials and Processes*, McGraw-Hill, 1975). Negative photoresists combine a photoinitiator (e.g., a bisazide) with various resin systems including, for example, polyvinyl cinnamates, allyl esters and polyisoprenoids. Negative photoresists based on polyvinyl alcohol and stilbazolium salts have been described as well (see U.S. Pat. No. Curtis 5,445,916 and Ichimura et al., U.S. Pat. No. 4,891,300). Under appropriate conditions a diazoquinone photoresist can be made to function either positively, as noted above, or negatively using the same aqueous alkaline developer. This may be performed, for example, by patterned irradiation in a vacuum. The entire photoresist is then irradiated at ambient conditions. Regions not irradiated in vacuum are solubilized in aqueous alkaline developer yielding a negative image.

The photoresist may be reactive to infrared, electron beam, x-ray or any other irradiation. A suitable electron beam resist includes, for example, EB-9 polymethacrylate available from Hoya™. The photoresist may be, for example, a polymer, thermoplastic, dye-sensitized polymer, or dye-sensitized thermoplastic that may be photoablated at a particular wavelength of light. Such compounds include, for example, polycarbonate and polyethyleneterephthalate which may be photoablated either by infrared or ultraviolet radiation directly (see Sonnenschein and Roland, *Appl. Phys. Lett.* 57(5):425, 1990 and Oldershaw, *Chem. Phys. Lett.* 186:23, 1991). The conjugated organic polymers known as polydiacetylenes may be photoablated in the visible part of the spectrum (see Lemoire and Blau, *Microelectronics Eng.* 13:447, 1991). Alternatively, photoablation may be achieved using a polymer-dye composite where the dye assists in absorbing radiant energy of a particular wavelength. Such dyes include, for example, polyester yellow ([p-(dialkylamino) benzylidene] malononitrile), polymethine dyes, carbocyanine dye NK1748, and squarylium (see Law and Johnson, *J. Appl. Phys.* 54(9):4799, 1983; Murthy et al., *J. Appl. Polymer Sci.* 31:2331, 1986; Law and Vincett, *Appl. Phys. Lett.* 39(9) :718, 1981; and Jipson and Jones, *J. Vac. Sci. Technol.* 18(1):105), 1981. Other methods may be used including, for example, exposure to a current source. For example, organosulfur redox polymers may be electrically depolymerized into monomers (e.g., dimercapto dithiazole) exposing discrete regions of biologic material on a microfabricated electrode array (see Liu et al., *J. Electrochem. Soc.* 138(7):1896, 1991). It may be desirable in some embodiments to utilize one or more photoresists sensitive to different wavelengths of light so as to, for example, select different regions based on the regional application of photoresists to the substrate.

Photoresist may be applied using any suitable technique known in the art. For example, photoresist may be applied to the biologic material with a pipette, and allowed to drain by gravity by vertically positioning the substrate. Alternative methods of photoresist application will be apparent to those skilled in the art including dip-coating, spin-coating, microdispensing and the application of pre-formed sheets or films. Where the applied photoresist is a liquid mixture, the solvent is allowed to evaporate leaving an evaporated film. Evaporation of the solvent may be achieved most preferably by heating at a temperature between 80° C. and 130° C., preferably between 85° C. and 90° C., at about one atmosphere pressure, although other combinations of temperature and pressure will result in evaporation. A few minutes is generally sufficient for evaporation. Following this softbake, a substrate may be further baked for several minutes at 110° C. to 135° C. to ensure complete solvent removal. Incomplete solvent removal may lead to a coating that loses integrity upon contact with various solvents.

The resulting photoresist layer should be sufficiently thick to prevent detection of a substance of interest in the underlying biologic material under conditions that permit such detection in the absence of photoresist. The necessary thickness will vary depending of the type of photoresist and the type of analysis to be performed. Preferably, the evaporated photoresist thickness is less than 1000 $\mu$m, and most preferably between about 0.5 to 15.0 $\mu$m. The final thickness of the evaporated film may be controlled by altering the percent solids, molecular weight of the solids, viscosity, or the spin speed in the case of spin-coating. A relative decrease in film thickness results in a corresponding decrease in the preferred irradiation time. It will be noted that there is no restriction on the film thickness that may be applied so long as it is compatible with performing the desired analytic procedures on the biologic material. By making the film thickness sufficiently small, the preferred irradiation time can be minimized, resulting in a very rapid irradiation process. According to one embodiment, this may be achieved by diluting the photoresist with an organic solvent including, for example, 2-ethoxyethyl acetate, 1-methoxy-2-propyl acetate or 3-pentanone.

All operations in the process of applying, irradiating and developing the photoresist should be carried out in a room lit primarily or entirely by light of a wavelength outside of the light range which will react with the photoresist. In the case of a positive diazoquinone photoresist, for example, a protective golden shield or sleeve (Imtec Products Inc., Sunnyvale, Calif.) which blocks light less than 500 nm, may be placed over standard cool-white fluorescent lights.

E. Irradiation

Figure 3:
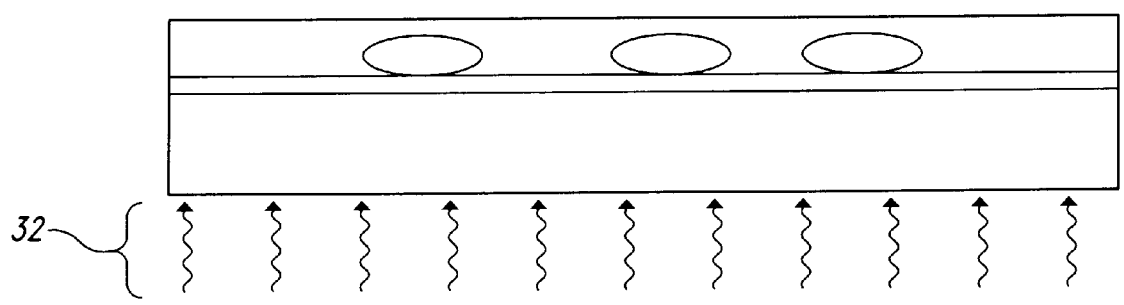
FIG. 3 is a cross-section diagram illustrating the illumination of the photoresist shown in FIG. 2 with a first light 32 to visualize and locate the biologic material, wherein the first light does not substantially react with the photoresist.

Prior to and/or during irradiation, a substrate may be illuminated with a light that has no substantial effect on the photoresist (see FIG. 3). Such illumination may be useful, for example, to visualize or locate regions of interest in the biologic material with or without the use of a stain or other technique to facilitate visualization. The biologic material is preferably stained, and visualized directly using optical microscopy. Alternatives to optical microscopy include, for example, indirect visualization using a charge coupled device (CCD), electrode, phosphor screen imager, electronic autoradiography (e.g., InstantImager®, Packard Inc., Meriden, Conn.), electron microscope, STM or AFM. The illumination may be directed at either the biologic material layered with photoresist, or the back of the substrate, so long as the substrate is transparent to the wavelength of light. A light with no substantial effect on the photoresist may be selected by choosing a wavelength of light that does not substantially react with the photoresist. In some instances, illumination may be achieved using a reactive wavelength, provided that substantial reaction with the photoresist is prevented through the use of an appropriate low intensity or short duration. Most preferably, the biologic material is illuminated on the back of the substrate using for illumination an incoherent light that is filtered with a long bandpass filter that passes 535–700 nm irradiation (e.g., a modet no. A43,386 long bandpass filter. Edmund Scientific Co., Barrington, N.J.).

Figure 4:
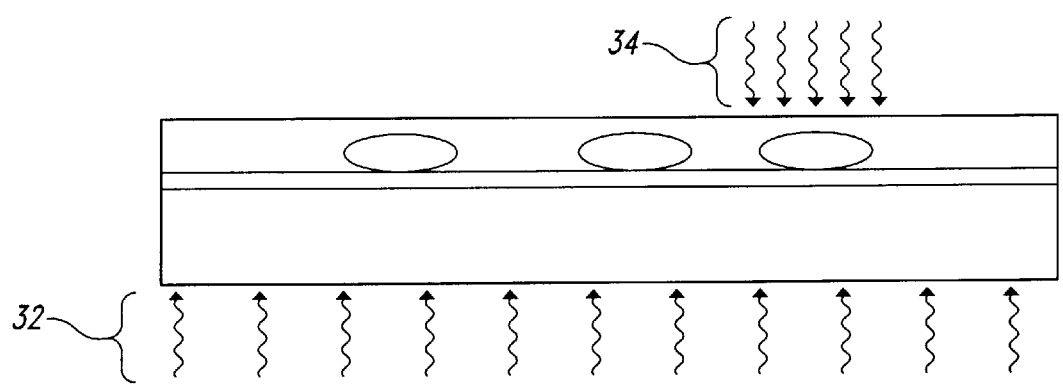
FIG. 4 is a cross-section diagram illustrating the irradiation of the photoresist shown in FIG. 2 with light 34, such that the biologic material is exposed in a first region.

As shown in FIG. 4, illumination and irradiation may take place simultaneously, preferably with irradiation targeting a sub-portion of the illuminated region. However, illumination and irradiation can function independently, and the substrate may be illuminated and irradiated at the same time, different times, same locations, different locations, or any combination of these.

With or without illumination, the photoresist layer is irradiated selectively (i.e., a portion of the photoresist is irradiated with a wavelength that alters the solubility of the irradiated region). In preferred embodiments, the photoresist layer is selectively irradiated with either 10×, 20× or 40× objective lenses, although the photoresist layer may be selectively irradiated with any type of optics. These objective lenses provide for a relative increase in Watts/cm$^2$ of 100×, 400× and 1600×, respectively. The relative increase in Watts/cm$^2$ results in a corresponding decrease in the irradiation time required for the photoresist to substantially react. It will be noted that there is no restriction on the Watts/cm$^2$ that may be applied so long as it is compatible with performing the desired analytic procedures on the biologic material. By making the Watts/cm$^2$ sufficiently large, the irradiation time can be made negligibly small, resulting in a very rapid irradiation process. Besides optically concentrating light, increasing the Watts/cm$^2$ may also be achieved by increasing the intensity of the light using, for example, a moderate to high powered laser (preferably 20 mW to 1000 mW). In preferred embodiments, the photoresist is a positive diazoquinone photoresist, for example AZ® 1500 series positive photoresist (Hoechst Celanese™, Somerville, N.J.), selectively irradiated for between 1 and 5 seconds with light from a 50 Watt mercury lamp focused with either a 10×, 20×, or 40× objective, and filtered with an excitation filter that passes about 400–440 nm irradiation. Preferably this is a modet no. BP400–440 excitation filter (Carl Zeiss, Thornwood, N.Y.).

Selective irradiation may also be achieved using one or more masks and photolithographic techniques of the type known in the semiconductor industry (see Sze, VLSI Technology, McGraw-Hill (1983), and Mead et al., Introduction to VLSI Systems, Addison-Wesley (1980)). Irradiation is preferably directed at the surface layered with the photoresist, but may also be directed at the back of the substrate, so long, as it is transparent to the wavelength of light needed to react with the photoresist. The photoresist may be irradiated either in contact or not in contact with a solution, and is preferably irradiated not in contact with a solution. Using the photolithographic methods disclosed herein, it is possible to mask light to very small and precisely known locations, thereby achieving a method with exemplary reproducibility and dimensional control consistent with the exposure of biologic, ic material in submicron regions.

A mask employed for the selective irradiation is generally an opaque support with transparent regions that allow the free passage of light to selected regions of the photoresist. Opaque regions may block light by absorbing or reflecting it. Within preferred embodiments, a single mask is used to simultaneously irradiate all regions. In some embodiments it is possible to use a single mask to irradiate different regions by translating and/or rotating the mask with respect to each of the regions. A mask may be, for example, a glass sheet having etched chrome thereon or a silver-halide film with opaque regions obtained by laser-photoplotting. Such masks are manufactured by, for example, Precision Image Corporation, Redmond, Wash.

The transparent regions of a mask are in a pattern substantially identical to the pattern of light that will irradiate the photoresist layer, and permit the passage of light in a pattern that corresponds to the irradiated regions. The transparent regions may be of any size or shape. For example, squares, ellipsoids, rectangles, triangles, circles, or portions thereof, along with irregular geometric shapes, may be utilized. In preferred embodiments, the area of each transparent region is extremely small being between about 1 cm and $10^{-12}$ cm$^2$, preferably less than 0.3 cm$^2$, and most preferably between about 1 $\mu$m$^2$ and 1 mm$^2$. For example, a transparent region may have an area less than about $10^{-1}$ cm$^2$, $10^{-2}$ cm$^2$, $10^{-3}$ cm$^2$, $10^{-4}$ cm$^2$, $10^{-5}$ cm$^2$, $10^{-6}$ cm$^2$, $10^{-7}$ cm$^2$ or $10^{-8}$ cm$^2$. In preferred embodiments, a mask comprises a plurality of transparent regions. In some embodiments, a mask comprises more than $10^2$, $10^3$, $10^4$, $10^5$, $10^6$, $10^8$ or $10^9$ separate transparent regions. In preferred embodiments, a mask comprises greater than 100 duplicates of an array of separate square or circular transparent regions, each array comprising greater than $10^3$, $10^4$, $10^5$ or $10^6$ transparent regions. It will be understood, of course, that the irradiated regions of a photoresist layer will have sizes, shapes and numbers that correspond to the transparent regions of the mask.

During irradiation, a mask is brought into close proximity with, imaged on, or preferably brought directly into contact with the photoresist surface. In alternative embodiments, the mask may be some distance away from the photoresist surface, as occurs in the technique known as projection printing. Alignment may be performed using conventional alignment techniques in which alignment marks are used to accurately overlay successive masks, or more sophisticated techniques may be used. For example, interferometric techniques may be used (see Flanders, *App. Phys. Lett.* 31:426, 1977). In some embodiments, a patterned porous coating may itself serve as an alignment mark.

With the mask appropriately positioned over the photoresist, the mask is irradiated with light. The light may be from a conventional incandescent source, a UV source, a laser, a laser diode, an excimer laser, an x-ray source, a programmable mask, a fiber optic or the like. In some embodiments, a positive photoresist layer as described in co-pending application entitled "Solvent-Resistant Photosensitive Compositions" may be irradiated with 365 nm light from a UV transilluminator manufactured by UVP Inc. (Upland, Calif.) at an energy density of 8 mW/cm$^2$ for sufficient time to permit substantial removal of irradiated photoresist by developer. In preferred embodiments, the photoresist is irradiated for between 8 and 12 minutes. Such radiation is not absorbed by the bonds typically found in molecules, obviating the possibility of directly photodegrading surface-attached molecules.

To enhance the contrast of light applied to the photoresist, contrast enhancement materials may be provided between the mask and the photoresist. A contrast enhancement layer may comprise a molecule that is decomposed by light or transiently bleached by light. Transient bleaching of materials allows greater penetration where light is applied, thereby enhancing contrast. Poor contrast due to standing waves and reflective notching may be reduced by applying an anti-reflective coating, for example, ARC® coating manufactured by Brewer Science Inc., Rolla, Mo. Alternatively, contrast enhancement may be provided by way of a cladded fiber optic bundle. The use of contrast enhancement materials is well known in the art.

As alternatives to the use of masks, other methods may be used to irradiate selected regions of photoresist. For example, the substrate may be translated under a modulated laser or diode light source (see Feyrer et al., U.S. Pat. No. 4,719,615). In alternative embodiments, a laser galvanometric scanner may be utilized. In other embodiments, the irradiation of the photoresist may take place on or in contact with a fiber optic light source, or a liquid crystal. By appropriately modulating liquid crystals, light may be selectively controlled so as to permit light to contact selected regions of the photoresist. Such a liquid crystal is also referred to as a "programmable mask," or an integrated circuit spatial light modulator (ICSLM), manufactured by Displaytech (Boulder, Colo.). Alternatively, irradiation may take place on the end of a series of optical fibers to which light is selectively applied. In some embodiments, light will be directed to extremely small regions, being limited by diffraction to a size directly proportional to the wavelength of light. In order to mask irradiation to regions smaller than a wavelength of light, more elaborate techniques may be utilized. For example, light may be directed at the photoresist by way of molecular microcrystals on the tip of, for example, micropipettes (see Lieberman et al., *Science* 247:59, 1990). Other means of controlling the location of light exposure will be apparent to those of skill in the art. Masking strategies are described in further detail below.

Figure 5:
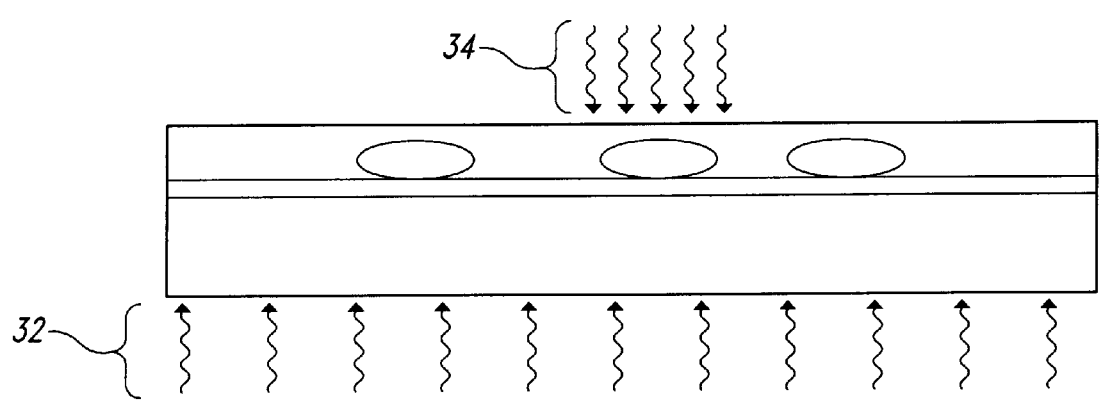
FIG. 5 is a cross-section diagram illustrating the irradiation of the photoresist shown in FIG. 2 with light 34, such that the biologic material is exposed in a different region.

The process of irradiating the photoresist may be repeated, if desired, until all regions of interest in the biologic material have been irradiated (see FIG. 5). Preferably, the irradiation is blocked by a manual or electronic shutter when the substrate is translated between non-contiguous regions of interest. Alternatively, this may not be required if a path is found between non-contiguous regions that is devoid of biologic material, or if the translation of the substrate is sufficiently fast so that transient irradiation of the photoresist between non-contiguous regions has no substantial effect on the photoresist.

In certain embodiments, the irradiation of the photoresist may itself result in substantial removal of the irradiated photoresist, generating exposed biologic material. Within other embodiments, the irradiated photoresist layer must be exposed to a developer to remove photoresist. The developer may be a solution that selectively solubilizes and removes irradiated or non-irradiated regions. In photoresist embodiments employing photoreactions that proceed by a non-crosslinking mechanism, developers may be identified by testing solvents and solvent mixtures that fall outside the solubility spectrum of the polymeric component. Often the photoactive component in such photoresists results in the production of a basic hydroxyl or carboxylic moiety and selective solubilization of irradiated portions can be achieved by the addition of an aqueous or organic base to the solvent or solvent mixture. Preferable organic bases include, for example, triethylamine, ethylamine, ethanolamine, triethanolamine, morpholine, piperidine, and diisopropylethylamine. Using these guidelines, selected solvent and base mixtures can be rapidly tested for developer activity in a panet format using several coated substrates irradiated in parallel through a test mask pattern.

For photoresists based on photo-crosslinking, preferable developer solutions are most readily identified by testing solvents that are known to be within the solubility profile of the polymeric component. Suitable developers comprise aqueous and non aqueous mixtures of solvents containing ketone, amino, hydroxyl and/or amide moieties, such as N-methylpyrrolidone, dimethylacetamide or dimethylformamide. For example, a negative photoresist of the cyclized polyisoprenoid variety may be developed with xylene.

In general, the substrate should be allowed to remain in contact with a developer solution until the photoresist coating has been substantially removed from irradiated regions of a positive photoresist (or non-irradiated regions of a negative photoresist). Numerous methods of contacting a developer with the irradiated photoresist exist, including immersion, spraying, puddling and streaming.

In preferred embodiments employing a positive photoresist layer as described in co-pending application entitled "Solvent-Resistant Photosensitive Compositions," substantial removal of irradiated photoresist requires from 5 to 10 minutes of immersion in a nonaqueous developer comprising a mixture of organic solvents.

In preferred embodiments utilizing a positive diazoquinone photoresist, substantial removal of irradiated photoresist requires from 10 to 300 seconds of immersion in an aqueous alkaline developer. The aqueous developer solution has an alkaline pH preferably in the range of 9 to 12 and preferably about 11, and contains various buffering systems well described in the patent literature and known to those skilled in the art. The rate of irradiated photoresist dissolution can be increased with increasing pH and temperature limited mainly by solubility considerations of non-irradiated areas. In a preferred embodiment, the substrate is immersed in developer solution, preferably AZ® 351 Developer (Hoechst Celanese™, Somerville, N.J.) diluted six-fold with water, preferably for about 30 to 60 seconds, preferably at a temperature ranging from 20° C. to 30° C. and most preferably at a temperature ranging from 23° C. to 27° C. The temporal progress of dissolution is visually monitored by the formation of red dye from irradiated regions during the development process. Not wanting to be limited by theory, the dye is thought to form by the reaction of indene carboxylic acid (IV) with unreacted diazoquinone. It has been discovered that the alkaline developer provides the additional advantage of destaining the biologic material; an important advantage as stains are inhibitors of certain analytical reactions including PCR.

After completion of exposure to developer, the photoresist layer may be rinsed with a suitable volatile solvent so as to remove residual developer and/or removed photoresist. One suitable rinse solvent for positive photoresist layers as described in co-pending application entitled "Solvent-Resistant Photosensitive Compositions" is acetonitrile. A suitable rinse solvent for a positive diazoquinone photoresist is water. A post-rinse heat treatment or bake may be employed to further increase the solvent-resistance of the film. In some embodiments, the film is heated at a temperature from about 90° C. to 135° C. for about one minute.

Figure 6:
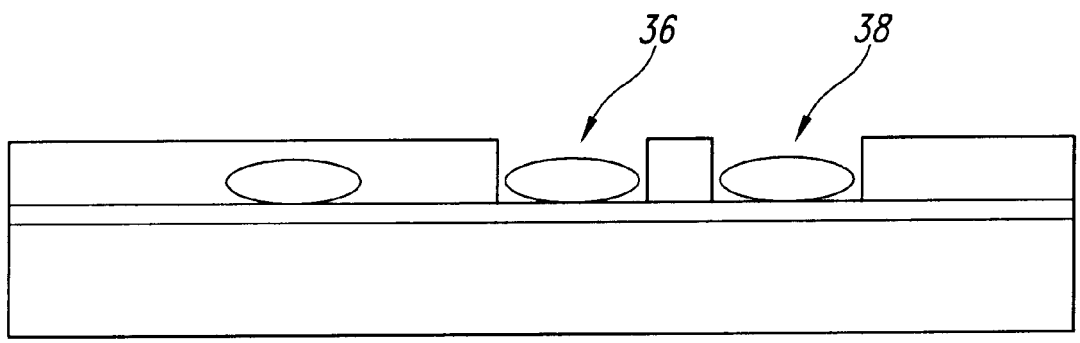
FIG. 6 is a cross-section diagram illustrating the irradiated substrate shown in FIG. 5 following contact with developer.

A preferred embodiment is illustrated in FIG. 6. Following the process of irradiating all regions of interest, the entire substrate is contacted with a developing solution, resulting in dissolution and removal of photoresist from irradiated regions 36 and 38. FIG. 6 illustrates the process with a positive photoresist, but it will be apparent that in the case of a negative photoresist, dissolution and removal of photoresist will be in non-irradiated regions.

The process of irradiation results in the generation of a substrate on which a biological material is immobilized, wherein the biological material is partially coated with photoresist. In other words, at least one region of the biological material is coated with photoresist, and at least one region of biological material is not so coated. As noted above, the number and size of such regions may vary. In general, however, at least one region having a diameter of at least $10^{-12}$ cm$^2$ is coated, and at least one region having a diameter of at least $10^{-12}$ cm$^2$ is uncoated.

F. Ablation

The step of irradiation described above is sufficient to expose biologic material underlying regions of the removed photoresist. If the exposed region(s) are the regions of interest for analysis, such analysis may be initiated without further sample preparation. In some instances, however, it is desirable to alter the exposed biologic material so as to inhibit detection of a substance of interest in such regions. Such alteration is referred to herein as ablation. Following ablation, photoresist may be removed, and analyses may be performed using the remaining regions of biologic material that were protected from ablation by the photocresist coating.

Ablation may be achieved using any technique that is suitable for altering the particular substance of interest. For example, the biologic material may be substantially destroyed by exposure to extreme radiation (such as from an excimer laser or reactive ion etch system) or chemicals capable of causing substantially complete destruction (such as strong acids (e.g., hydrofluoric acid), strong bases (e.g., concentrated NaOH), peroxides ($H_2O_2$) and mixtures thereof). Alternatively, the alteration may be relatively mild, resulting in only chemical modifications (which may be specific or nonspecific) of molecules in the biologic material. For example, glutaraldehyde nonspecifically modifies amino moieties through covalent coupling without substantially destroying the biologic material. In some cases the alteration will be relatively specific for a particular class of molecules within the biologic material. For example, nucleases will specifically destroy nucleic acids within biologic material while leaving other classes of biologic molecules substantially intact. In some embodiments, the alteration will be a physical, rather than a chemical, modification. For example, a high-pressure water stream or consecutive ultrasonic pulses directed at a biologic material may be used to detach, disrupt and/or discard the biologic material from a substrate surface where a particular detection reagent or assay is to be performed without causing any chemical change to the biologic material per se. Other suitable alterations which may be applied to biologic material to eliminate a detectable response will be apparent to those of skill in the art. The magnitude of the alteration which must be applied to eliminate an expected detectable response will be readily determined by testing a given alteration at various magnitudes against a representative substance of interest and determining at what magnitude there is no longer a detectable response. For example, Shibata et al. provides teaching for determining the duration and intensity of ultraviolet light which must be applied to tissue sections to render them incapable of providing a detectable response in a PCR reaction (see Shibata et al., *Am. J. Pathol.* 141:539, 1992).

It will be apparent that a variety of ablative agents may be contacted with exposed biologic material to effect ablation. Ablative agents include oxidants, free radicals, non-specific nucleases, non-specific ribonucleases, peptide nucleic acid clamps, high energy particles, extremes of radiation, ultrasonic energy, high pressure liquids, ultraviolet irradiation and combinations thereof. In general, to achieve ablation, exposed biologic material is contacted with an ablative agent, under conditions and for a time sufficient to alter any substance of interest present within the exposed biologic material, such that the substance of interest is not detectable in the exposed biologic material. Ablation conditions may be readily optimized using routine testing, in which exposed biologic material is assayed for the substance of interest following ablation.

Following ablation, photoresist is removed from the remaining biologic material, exposing the remaining material for analysis. The solvent profile of the photoinactive polymer component allows suitable strippers to be readily identified by those of skill in the art. In the case of photoresists that proceed by a non-crosslinking mechanism, the final photoresist typically is stripped using solvents that solubilize the polymeric component. Such solvents are typically unreactive and cause no adverse changes in the underlying biologic material. In preferred embodiments, a suitable stripping solution is selected from the group consisting of dimethylformamide (DMF), N-methylpyrrolidone (NMP), or dimethylacetamide (DMAC). Photoresists based on the following preferred polymers will typically be stripped by the indicated solvents:

polyethylene (low density) halogenated hydrocarbons
polypropylene clorinated hydrocarbons
poly(di-n-butyl itaconate) THF
polyacrylamide morpholine, water
poly(vinyl alcohol) water, DMF
poly(ally alcohol) methanol, THF
poly(chlorotrifluoroethylene) —$CCl_4$
poly(oxypropylidene DMF
poly(2,5-dimethoxy-1,4-phenyleneethylene bromoform
poly(oxy-1,4-phenyleneethylene m-terphenyl
poly(1-butane-co-sulfur dioxide acetone
poly(imino(1oxotrimethylene chloroacetic acid
poly(1,3,4-oxadiazoles) DMSO
poly(dibenzoxazole) M-cresol
poly(dithiazoles) DMF poly(pyromellitimides) dimethylactamide
poly(benzimidazoles) DMSO
poly(dibenimidazoles) N-methylpyrrolidone
polyamic acids N-methylpyrrolidone
polyimides N-methylpyrrolidone
polyphenolformaldehyde acetone For photoresists based on photo-crosslinking, stripping solutions are required that cleave the crosslinked polymeric network, but do not adversely affect the immobilized biologic agent. Such stripping solutions require agents which specifically cleave bonds in the polymeric network. For example, photoresists based on cross-linked polyvinyl alcohol may be selectively stripped using aqueous sodium periodate as long as the substance of interest in the biologic material lacks linkages comprising two or more —OH or =O groups attached to adjacent carbon atoms. Other selectively cleavable linkages in the polymer will be readily apparent to those of skill in the art.

The stripping process should substantially remove the entire photoresist layer. In other words, as noted above, the photoresist should be sufficiently removed to permit detection of a substance of interest in the underlying biologic material at a level that is at least 50% of the level observed for similar biologic material that has not previously been coated with photoresist. Stripping conditions may be readily optimized by routine testing, in which a test biologic material is assayed without photoresist coating and following coating and stripping.

H. Analysis

It will be apparent to those of ordinary skill in the art that exposed biologic material may be assayed by any of a wide variety of analytical techniques. Such assays include techniques in which the exposed biologic material is contacted with a detection reagent that generates a detectable response indicative of the presence or absence of a substance of interest in the exposed biologic material. This response is then detected using any suitable technique.

Detection reagents include any of a variety of molecules, including antibodies, nucleic acid sequences and enzymes. To facilitate detection, a detection reagent may comprise a marker, such as a chromophor, fluorophor or radionuclide. Markers may be detected based on, for example, color, absorption of electromagnetic radiation, optical interference, electric conduction, radioactive decay, fluorescence, chemiluminescence, phosphorescence, or a molecular shape detectable by scanning tunneling microscopy (STM) or atomic force microscopy (AFM). Any of a variety of assays may be used to detect a signal from the detection reagent, including (but not limited to) electrophoresis, chromatography, mass spectrometry, DNA sequencing, peptide sequencing, nucleic acid hybridization and PCR.

As noted above, within certain embodiments, the methods provided herein may be used to screen for receptor binding to ligand arrays. For example, such arrays can be used to determine peptide and nucleobase sequences that bind to proteins or nucleic acids, identify epitopes recognized by antibodies, evaluate a variety of drugs and metabolites for clinical and diagnostic applications, and screen small-molecule libraries for novet drugs, pesticides, or herbicides, as well as combinations of the above. In embodiments in which the ligand and receptor are both polymers, the sequence of the polymer at the locations where the receptor binding is detected may be used to determine all or part of a sequence which is complementary to the receptor. Of course, it is also possible to screen for ligand-receptor binding using receptor arrays, rather than ligand-arrays, using the methods provided herein.

It will be apparent that the type of ligands that may be screened is without restriction. In preferred embodiments the ligands may include, for example, potential pharmacologic, pesticide, or herbicide candidates, drug analogues, or important biologic polymers including DNA, PNA, PENAM and other nucleobase polymers. Ligand arrays may be prepared by any suitable method, including the methods provided in copending application "Methods and Compositions for Performing an Array of Chemical Reactions on a Support Surface."

Certain preferred ligands are nucleobase polymers. A nucleobase polymer is a polymer of nucleobases linked to a backbone. The backbone may be naturally occurring or non-naturally-occurring. Nucleobases linked to such a backbone may be naturally-occurring or non-naturally-occurring. Such nucleobase polymers may be capable of hybridizing specifically to particular nucleic acid sequences (e.g., antisense molecules). Besides resistance to degradative enzymes, some arrays of nucleobase polymers offer additional advantages. For example, PNA arrays provide for more rapid hybridization, greater specificity, more convenient hybridization conditions (i.e., hybridization of short probes at higher temperatures) and the ability to hybridize duplex DNA directly via DNA strand displacement and triplex formation.

A further advantage of many nucleobase polymers is the ability to penetrate the membranes of living cells. In embodiments employing nucleobase polymers capable of permeabilizing cell membranes, arrays can be used to modulate gene expression in an antisense manner. Within such embodiments, each nucleobase polymer of the array is detached from the substrate while in contact with one or more living cells, preferably using an enzyme-labile linker as described herein.

Representative examples of suitable nucleobase polymers include peptide nucleic acids (see Buchardt et al., PCT WO 92/20702 and Buchardt et al., U.S. Pat. No. 5,719,262), which offer a number of advantages over DNA including stronger binding independent of salt concentration (i.e., a hither $T_m$ than a corresponding DNA probe), greater specificity of interaction, reduced hybridization times and resistance to environmental nucleases. Under low salt conditions, PNA binding is so energetically favorable that it binds duplex DNA directly by displacing one strand of the duplex. Other suitable nucleobase polymers include morpholino-based nucleobase polymers (see Summerton and Weller, U.S. Pat. No. 5,698,685; Summerton et al., U.S. Pat. No. 5,378,841 and Summerton and Weller, U.S. Pat. No. 5,185,444), peptide-based nucleic acid mimics or PENAMs (see Shah et al., U.S. Pat. No. 5,698,685), and polynucleosides with linkages comprising carbamate (see Stirchak and Summerton, *J. Org. Chem.* 52:4202, 1987), amide (see Lebreton et al., *Synlett. February* 1994:137, 1994), methylene(methylimino) (see Vasseur et al., *J. Am. Chem. Soc.* 114:4006, 1992), 3'-thioformacetal (see Jones et al., *J. Org. Chem.* 58:2983, 1993), sulfamate (see Huie and Trainor, U.S. Pat. No. 5,470,967) and others (see Swaminathan et al., U.S. Pat. No. 5,817,781 and Freier and Altmann, *Nucl Acids Res.* 25:4429, 1997 and references cited therein). Particularly preferred nucleobase polymers contain repeating units as indicated below, where B is a naturally-occurring nucleobase or a non-naturally-occurring nucleobase:

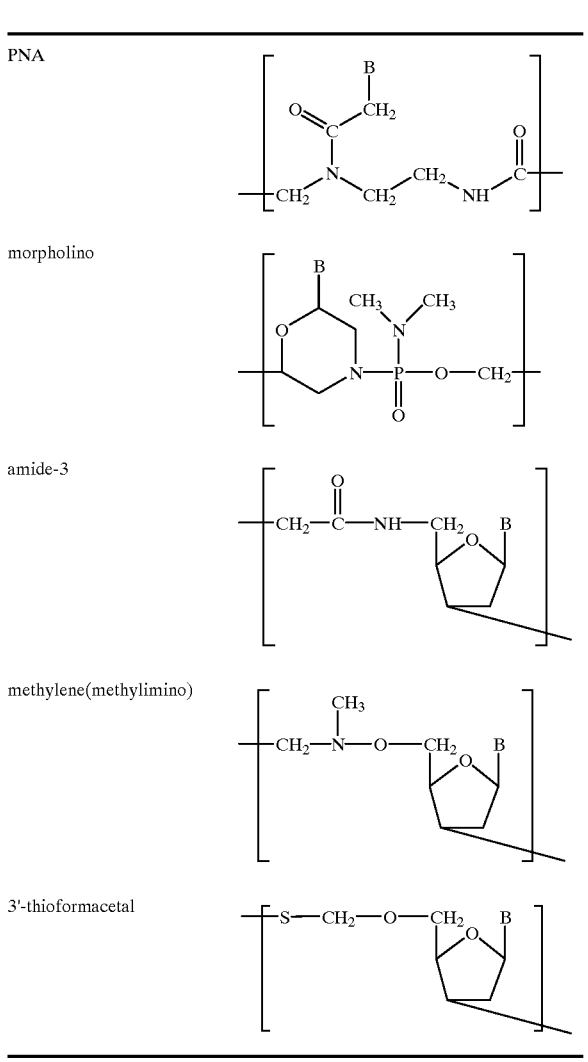

Other suitable nucleobase polymers will be readily apparent to those of skill in the art.

Additional representative nucleobase polymers include those comprising a morpholino subunit of the form:

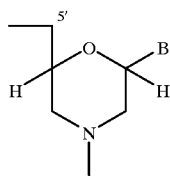

wherein (i) the subunits are linked together by uncharged phosphorus-containing, chiral linkages, one to three atoms long, joining a morpholino nitrogen of one subunit to a 5', exocyclic carbon of an adjacent subunit, and (ii) B is a nucleobase. Other nucleobase polymers may comprise a repeating unit of the form:

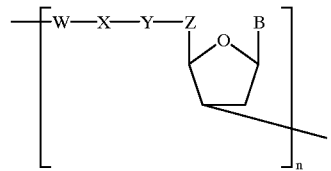

wherein each W is independently selected from the group consisting of —$CH_2$—, —O—, —S—, —CH=, —CO— and —$NR_1$—, wherein $R_1$ is hydrogen or a spacer; each X is independently selected from the group consisting of —$CH_2$—, —O—, —S—, —CH=, =CH—, =N—, —CO—, —$NR_2$—,

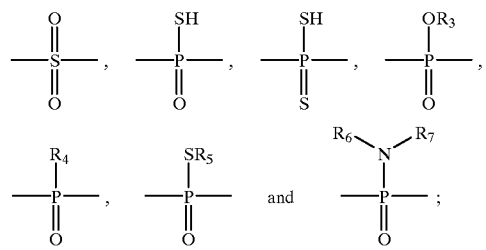

(wherein $R_2$ is hydrogen or a spacer, $R^3$ is alkyl or a spacer, $R_4$ is alkyl, cyanoethyl or a spacer group, $R_5$ is hydrogen or a spacer, $R_6$ is hydrogen or a spacer group, and $R_7$ is hydrogen or a spacer); each Y is independently selected from the group consisting of —$CH_2$, —O—, —S—, —CH≡, —CH=, =CH—, =N—, —CO— and —$NR_8$—, wherein $R_8$ is hydrogen or a spacer; each Z is independently selected from the group consisting of —$CH_2$—, —O—, —S—, =CH—, —CO— and —$NR_9$—, wherein $R_9$ is hydrogen or a spacer; each B is independently selected from the group consisting of nucleobases; and each n is an independently selected integer ranging from 1 to 100. Other representative ligands include linear and cyclic polymers of nucleic acids, polysaccharides, phospholipids, and peptides having either α—, β—, or ω-amino acids, polyesters, polycarbonates, polyureas, polyamides, polyethyleneimines, polysiloxanes, polyimides and polyacetates.

In certain embodiments, an array may comprise ligands that are drug candidates, preferably greater than 500 different drug candidates. Each drug candidate is preferably attached to the surface in quantities sufficient for screening using functional assays. Certain arrays comprise enaprilat analogues having the formula:

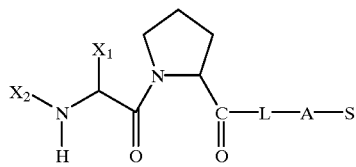

wherein S is the surface, A is aminopropyltriethoxysilane, L is a divalent linker molecule, $X_1$ is a monovalent organic group or hydrogen, and $X_2$ is a monovalent organic group or hydrogen. $X_1$ and $X_2$ may, within certain embodiments, be acid labile protecting groups.

To use a ligand-array to identify ligands that bind a specific receptor, the array is first contacted with a receptor of interest under conditions and for a time sufficient to permit receptor-ligand interaction, immobilizing the receptor. Following such contact, any of a variety of methods may be used to determine whether any ligands attached to the array specifically bind the receptor.

As noted above, there are a variety of biologic materials that may be used as receptors within such assays, including nucleic acid molecules, polypeptides, peptides, PNA, enzymes, enzyme cofactors, lectins, sugars, polysaccharides, antibodies, cell receptors, phospholipid vesicles, or any one of a variety of other receptors. Alternatively, a receptor may be a biological structure such as a cell, cellular membrane or organelle. A receptor may bind with zero, one or more ligands on the array. In some embodiments, a receptor may be from blood obtained from either healthy or diseased subjects, and screening an array for binding by the receptor may have diagnostic applications.

A receptor may be contacted with an array by placing an aliquot of a receptor solution directly on the array. Optionally, a microscope cover-slip is then placed on the receptor solution. In other embodiments, a receptor solution may be applied while the array is mounted to a reactor system as described herein. Alternatively, an entire array may be immersed in a receptor solution. In addition to receptor, receptor solutions may contain one or more buffers, salts, protein, nucleic acid, detergents, cofactors, polyelectrolytes and/or other such materials necessary for a particular receptor to bind ligand.

During contact, it may be important to maintain a specific temperature of the array. For example, temperature can influence the stringency of DNA, PNA, and RNA interactions such that specific binding to particular array elements will only be observed in a narrow temperature range. In other cases, a particular temperature may be required for a receptor to either adopt a needed conformation, or avoid thermal denaturation. An optimal temperature for performing an assay may be readily determined by those of ordinary skill in the art. Methods for maintaining the ligand-derivatized support at a particular temperature include, for example, placing the support in contact with a heating block, thermo-electric (Peltier) device, heated water bath, convection oven, refrigerator, freezer, or temperature controlled reactor system. In some embodiments, the substrate is mounted on a microscope stage that contains an aqueous get within its interior chilled to a specific temperature. Other methods for controlling the temperature of the ligand-derivatized support during contact with a receptor will be apparent to those skilled in the art.

Following contact, photoresist is applied and irradiated as described herein. If desired, an ablation step, followed by removal of the photoresist, may be performed. The presence of bound receptor is then detected using any suitable assay, which may involve the detection of a marker that permits determination of the location of bound receptor on the array. Suitable markers are well known in the art, and include radionuclides and fluorescent molecules. Markers may indicate the presence of ligand-receptor pairs by producing, for example, a differential color, absorption of electromagnetic radiation, optical interference, electric conduction, radioactive decay, fluorescence, chemiluminescence, phosphorescence, or a molecular shape detectable by scanning tunneling microscopy (STM) or atomic force microscopy (AFM), either by themselves or via other covalently and non-covalently linked molecules, labels, nuclear isotopes, antibodies, or enzymes. In some embodiments the ligand-receptor pair may produce a phenotypic change including, for example, cessation of cell growth, initiation of cell growth, apoptosis or cellular differentiation. Other methods of locating and visualizing ligand-receptor pairs will be apparent to those skilled in the art.

A ligand-array may be exposed only to a labeled receptor. Alternatively, an array may be exposed to a first, unlabeled receptor of interest and, thereafter, exposed to a labeled receptor-specific recognition element, which is, for example, an antibody. Such a process provides for additional amplification of signal during detection. In yet another embodiment, a multi-labeling scheme may be employed whereby the ligand-derivatized support is exposed to several different receptors, each coupled to a different label. A set of images, each representing the surface density of a particular label can be generated using spectral deconvolution methods well known in the art. Such multi-labeling strategies have a variety of uses. For example, the microenvironment of the sample may be examined using special labels whose spectral properties are sensitive to some physical property of interest. In this manner, pH, dielectric constant, physical orientation, and translational and/or rotational mobility may be determined.

In other embodiments, an indicator compound is added that indirectly detects ligand-receptor binding. An indicator compound refers to a compound that has a detectable property in the presence of a receptor that is different when the receptor is bound by a ligand. Such detectable properties include color, light absorbance, light transmission, fluorescence, fluorescence resonance energy transfer, fluorescence polarization, phosphorescence, catalytic activity, molecular weight, charge, density, melting point, chromatographic mobility, turbidity, electrophoretic mobility, mass spectrum, ultraviolet spectrum, infrared spectrum, nuclear magnetic resonance spectrum, elemental composition and X-ray diffraction. In one embodiment, the indicator compound furylacryloylphenyalanylglycylglycine (FAPGG) is used to detect binding of angiotensin converting enzyme (ACE) by an array of enalaprilat analogues. Hydrolysis of FAPGG by ACE results in a decrease in absorbance at 328 nm. The decrease in absorbance is attenuated if ACE is bound by an enalaprilat analogue. Other indicator compounds will be readily apparent to those skilled in the art.

REACTOR SYSTEMS

It will be apparent that a variety of devices, or reactor systems, may be used to achieve irradiation, as described herein. Certain reactor systems are also designed to achieve analysis of biologic materials following irradiation. Reactor systems provided herein have numerous advantages over existing devices. For example, the apparatus may be used to eliminate the need for transfer of material from the slide surface to a reaction tube, thereby obviating cumbersome and costly automation and robotics or the need for a specially prepared substrate. This feature further provides for superior sensitivity and sample purity with significantly reduced potential for contamination with non-irradiated tissue fragments, which is a significant advantage when sensitive amplification methods are employed (e.g., PCR). The apparatus further may be used to select biologic material with light, and in some embodiments a relatively small wavelength of light, thereby achieving superior resolution capabilities. The irradiation may be incoherent radiation, which is less costly that coherent radiation (e.g., laser irradiation in LCM), while providing superior contrast between irradiated and non-irradiated regions (e.g. no ragged borders as in LCM).

A reactor system may be made from any of a variety of materials, including biological, nonbiological, organic or inorganic materials, or a combination of any of these. For instance, the reactor system may be made of the same material as the substrate, for example, it may be of functionalized glass, Si, Ge, GaAs, GaP, $SiO_2$, $SIN_4$, modified silicon, photoresist, biolayers and silane layers (see Cozzette, U.S. Pat. Nos. 5,200,051 and 5,466,575; and Ribi, U.S. Pat. No. 5,156,810), or any one of a wide variety of gels or polymers such as (poly)tetrafluoroethylene, (poly)vinylidenedifluoride, polystyrene, polycarbonate, or combinations thereof. Other reactor system materials will be readily apparent to those of skill in the art upon review of this disclosure. In a preferred embodiment the body is a nylon cylinder and the separable cover is a flat sheet of clear plastic with an adhesive surface.

Figure 7:
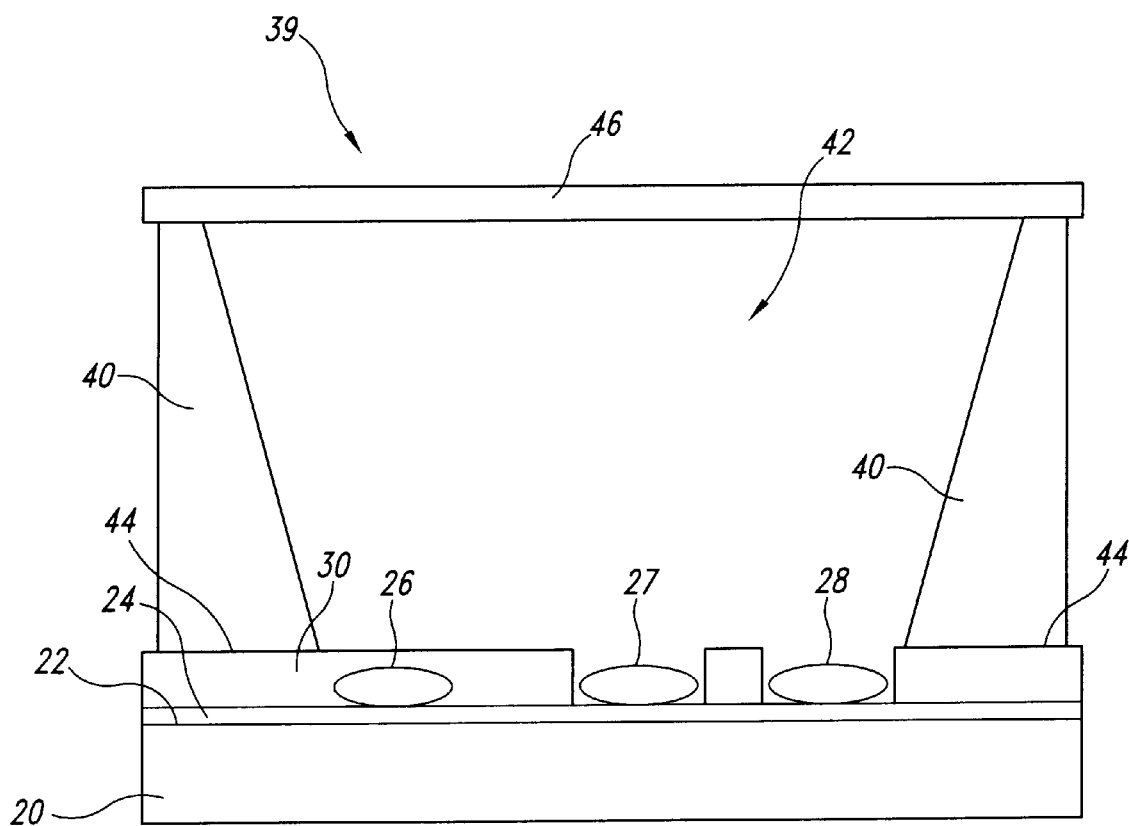
FIG. 7 is a cross-section diagram illustrating an embodiment of a reactor system for the regional analysis of the biologic material.

The reactor system may have any convenient shape, such as a disc, square, sphere, circle, or any irregular shape, so long as it contains a cavity topologically in contact with the exposed biologic material. The reactor body is preferably cylindrical with interior walls sloping towards the center, as depicted in FIG. 7, so as to facilitate working with small volumes of fluid in the chamber. Although the reactor system preferably forms a rigid body and chamber in which to carry out analytical reactions, the reactor system may be flexible being formed by, for example, Langmuir-Blodgett films, synthetic membranes, dialysis membranes or any flexible version of the material discussed above.

According to a preferred embodiment, the reactor system size is preferably about 1.5 cm in its greatest dimension, although it is readily understood that the reactor system could be of any size. Accordingly, the reactor system could be very small, for example, the reactor system could be micro-fabricated using micro-machining, photolithography, anodic-bonding, and other micro-fabrication methods known to those skilled in the art. According to a preferred embodiment, a nylon cylinder is mated to the photoresist surface with a silicone adhesive (Dow-Corning, Midland, Mich.), but other methods for mating the body of the reactor system to the photoresist are available, including other adhesives, epoxies, gaskets, sealants and clamps.

FIG. 7 schematically illustrates one embodiment of a reactor system 39 which provides for the analysis of exposed biologic material 27 and 28, but not unexposed biologic material 26 which is blocked by a layer of photoresist. In accordance with one aspect of the invention, the reactor system includes a body 40 mated to a photoresist surface 44 creating a reaction chamber 42. The body and a separable cover 46 serve to seal the cavity. Although the invention herein is illustrated with a reactor system on surface 44 of the photoresist, this is not a required feature of the invention and other arrangements of the reactor system are available for the analysis of exposed biologic material 27 and 28 so long as chamber 42 of the reactor system is in topologic continuity with the exposed biologic material. For example, the reactor system may be within the substrate (e.g., by micro-fabrication), being connected to the exposed biologic material through a conduit. Alternatively, analysis may occur by placing the entire substrate within the cavity of a reactor system. For example, the entire substrate may be immersed in an analytic solution. The solution may also be part of an in situ assay (i.e., immunocytochemistry, fluorescent in situ hybridization, in situ PCR).

Although the invention herein is illustrated with a single reactor system on the surface of the photoresist, this is not a requirement of the invention, and other analytic, amplification, separation, detection, or semiconductor systems may be connected with the reactor system described in this disclosure. Preferably, these systems will be relatively small, manufactured as described above using microfabrication methods. For example, other microfabricated systems which might be connected to the reactor system include electronic circuitry, capillary electrophoresis (see Woolley et al., *Proc. Natl. Accid. Sci. USA* 91:11348, 1994), PCR (see Wilding et al., Clin. Chem. 40:1815, 1994), probe hybridization (see Fodor et al., *Nature* 364:555, 1993), signal detection (see Lamture et al., *Nucl. Acids Res.* 22:2121, 1994), and microfluidic manipulation (see Burns et al., *Proc. Natl. Acad. Sci. USA* 93:5556, 1996).

The present invention provides a method and apparatus with numerous advantages. Certain reactor systems have the important advantage that the biologic material does not have to be removed from the substrate to a separate reaction vessel. In effect, the reactor system becomes a "reaction tube." This aspect of the invention, and the ability to select regions of interest with light, together provide significant advantages compared to removing biologic material from the substrate. These include superior accuracy, sensitivity, sample purity, resolution, contrast, selection speed, and simplicity of process automation. For example, with the apparatus described herein, both the selection of biologic material and the manipulation of fluids in the reactor system may be readily automated using commercially available equipment. The selection of biologic material may be performed using relatively inexpensive and commercially available equipment including a motorized x/y translation table, microscope, CCD and appropriately programmed computer. Similarly, the manipulation of fluids in the reactor system may be readily automated using, for example, a robotic liquid handling system such as MultiPROBE™ Robotic Liquid Handling Systems manufactured by Packard Inc. (Meriden, Conn.).

REPRESENTATIVE IRRADIATION TARGETING DEVICE

Any apparatus capable of targeting irradiation to a photoresist layer on a biologic material may be used to perform the methods provided herein. A preferred apparatus comprises: (a) a body capable of immobilizing a substrate; (b) a first electromagnetic radiation source that generates a first radiation for illumination purposes; (c) first optics that transform the first radiation to a first geometry having a first focal plane on the biologic material; (d) collection optics that receive response radiation from the biologic material; (e) a detector that generates a signal proportional to the amount of radiation received by the collection optics, such that the signal represents an image associated with the biological material: (f) a second electromagnetic radiation source that generates a second radiation that differs substantially in wavelength from the first radiation, such that the second radiation reacts with the photoresist; (g) second optics for transforming the second radiation to a second geometry having a second focal plane on the photoresist; and (h) a focuser that controls the height of the first and second focal planes. The second electromagnetic radiation source may be, for example, a mercury lamp. The apparatus may further comprise an attenuator, such as a shutter, that blocks transfer of second radiation to the photoresist. Alternatively, or in addition, the apparatus may further comprise a processor for processing and storing signal from the detector and coordinating the attenuator and the focuser to permit irradiation of a substrate at the plurality of defined regions.

Figure 8:
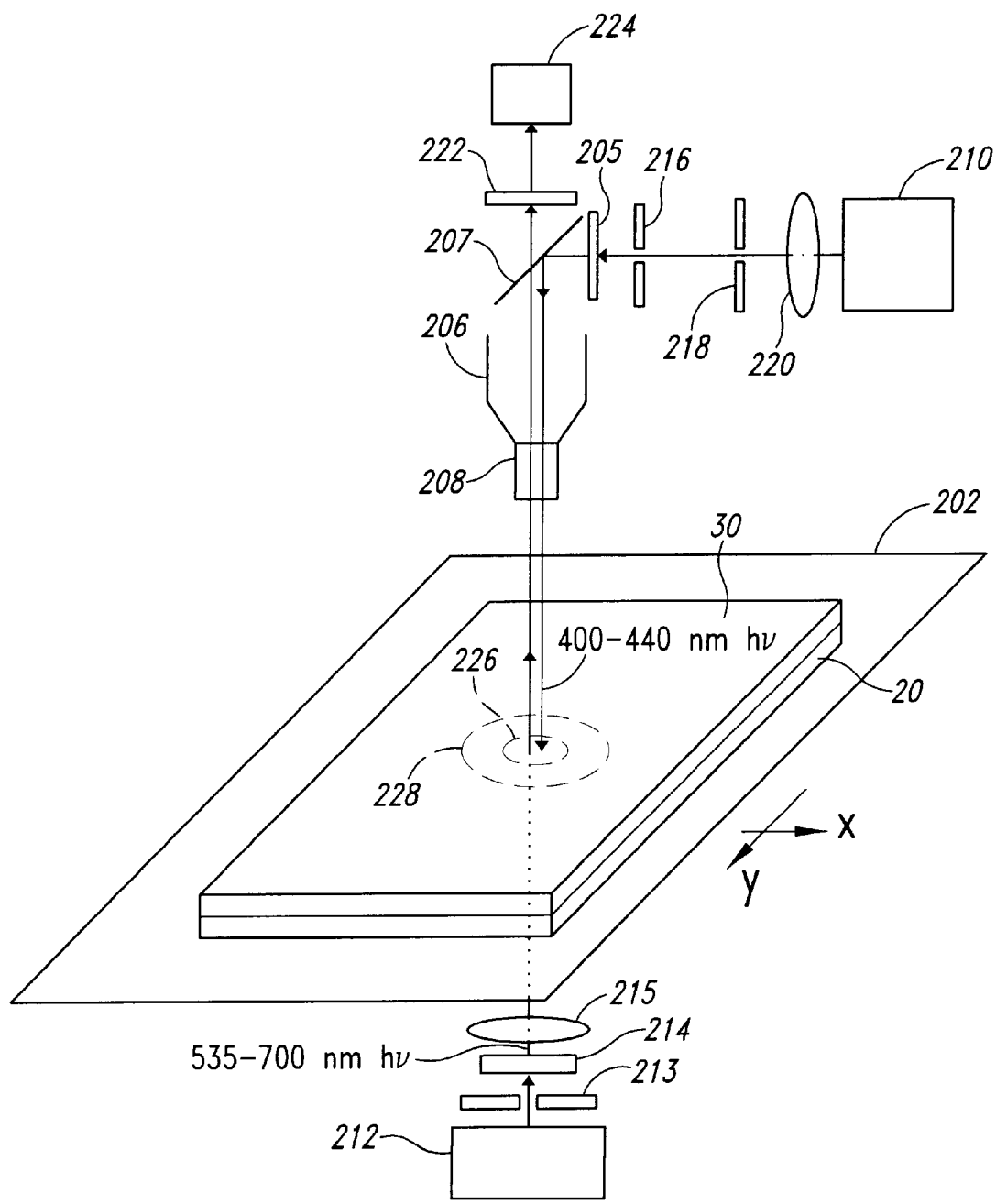
FIG. 8 is a cross-section diagram illustrating an embodiment of an irradiation targeting device.

FIG. 8 illustrates an irradiation-targeting device for visualizing and irradiating discrete regions of photoresist. Substrate 20, on which biologic material is immobilized and coated with photoresist 30, is placed on a manually operated x/y translation table 202. The substrate and x/y translation table are under a microscope 206 which includes one or more objectives 208. The x/y translation table, microscope and objectives may all be members of, for example, a Standard Microscope (Carl Zeiss, Thornwood, N.Y.).

A. Visualization

Light from a first lamp 212 is passed consecutively through an iris diaphragm 213, a long bandpass filter 214, and a condenser 215 to transilluminate substrate 20 in an area 228. Lamp 212, iris diaphragm 213, and condenser 215 are components of, for example, a Standard Microscope equipped with a 100 Watt halogen lamp, model no. 380059-1660 (Carl Zeiss). The long bandpass filter (e.g., a model no. A43,386, Edmund Scientific Co., Barrington, N.J.) passes 535 nm to 700 nm light from the first lamp. Light from transilluminated area 228 is collected by objective 208 and microscope 206 and directed to a dichromatic beam splitter 207. The dichromatic beam splitter (e.g., a model FT460, Carl Zeiss) passes greater than about 470 nm light, reflecting light less than this. Thus, the 535 nm to 700 nm light from first lamp 212 passes through the dichromatic beam splitter, and is directed to a barrier filter 222. The barrier filter (e.g., a model LP470, Carl Zeiss) passes greater than about 470 nm light to ocular optics 224 for visualization by a user.

B. Photopatterning

Light from a second lamp 210 is passed consecutively through a lamp condenser 220. an iris diaphragm 218, an open mechanical shutter 216, and an excitation filter 205. The second lamp, condenser, iris diaphragm, and mechanical shutter may all be members of, for example, a Vertical Illuminator IV FL fitted with a 50 Watt mercury lamp (Carl Zeiss). The excitation filter (e.g., a BP400–440 excitation filter, Carl Zeiss) passes 400 nm to 440 nm light from second lamp 210. Light passed by excitation filter 205 is directed at dichromatic beam splitter 207. The dichromatic beam splitter passes greater than about 470 nm light, reflecting light less than this. Thus, 400 nm to 440 nm light passed by excitation filter 205 is reflected 90 degrees by dichromatic beam splitter 207. Light from the dichromatic beam splitter is collected by microscope 206 and objective 208 and directed to substrate 20 forming an epi-illuminated area 226 on photoresist 30.

C. Operation of the Visualization and Photopatterning Subsystems

Long bandpass filter 214 functions to provide transillumination of substrate 20 with a wavelength of light that does not substantially react with photoresist 30 in area 228. The photoresist is translucent allowing the user to visualize and locate regions of interest in the biologic material using x/y translation table 202 without concern for causing a reaction in photoresist 30. In a preferred embodiment utilizing diazoquinone positive photoresist, long bandpass filter 214 does not pass light substantially below 500 nm. However, other embodiments using photoresists with different photochemical properties require alternative combinations of bandpass filter 214, excitation filter 205, and dichromatic beam splitter 207. Such combinations will be readily apparent to those skilled in the art upon review of this disclosure.

Excitation filter 205 functions to provide epi-illumination of substrate 20 with a wavelength of light that substantially reacts with photoresist 30 in area 226. The process of photoresist epi-illumination is benefited in a preferred embodiment by two unique properties of the diazoquinone photoresist. First, epi-illumination of the diazoquinone photoresist results in 510 nm to 560 nm fluorescence in area 226 which is visualized as a red circle within area 228. This allows the user to identify the size and borders of the region being photopatterned concurrently with visualization of area 228. Second, the photochemical reaction produces nitrogen gas which may be visualized as microscopic bubbles within photoresist layer 30 in area 226. The formation of microscopic bubbles is a convenient visual indicator of the temporal progress of the photochemical reaction within photoresist layer 30. It will be understood, however, that such visual indicators are not necessary components of the invention described herein, and may not be available in other photoresist systems.

Although regions 226 and 228 may be of any size or shape, region 228 is preferably a circle that occupies an objective's full field-of-view. In contrast, region 226 is preferably a circle of variable size. The size of region 226 is adjusted using iris diaphragm 218 according to the size and shape of the desired photopattern. For example, the photopattern size may encompass thousands of cells, a single cell, or a subcellular component. The substrate is exposed to light from second lamp 210 when manual shutter 216 is open. However, the manual shutter is closed when the substrate is translated between discontinuous photopatterned regions. Thus, the process of visualization and photopatterning is achieved by manipulating x/y translation stage 202, iris diaphragm 218, and manual shutter 218 until all regions of interest in the biologic material have been irradiated. Virtually any shape can be substantially photopatterned using this process and a plurality of circled regions 226 of varying size.

Irradiation of different regions of the substrate may be achieved by moving the substrate relative to fixed light sources 212 and 210 using a manually operated x/y translation table. Alternatively, other methods for controlling the location of light exposure are available as previously noted, as well as automated methods for translating the substrate. For example, the irradiation-targeting device may be automated by adapting ocular optics 224 with a CCD, manual shutter 216 with an automated shutter, manual iris diaphragm 218 with an automated diaphragm, and manual x/y translation table 202 with a motorized x/y translation table (e.g., a model no. PM500-A1, Newport Corporation, Irvine, Calif.). These may then be interfaced to a personal computer appropriately programmed with commercially available software (e.g., "Lab Windows", National Instruments, Austin, TX or Image-Pro Plus™ with Stage-Pro™, Media Cybernetics, Silver Spring, Md.). Such a system would allow regions of interest to be selected manually from a digital image displayed on a computer monitor. Alternatively, computer algorithms may be developed to automatically select appropriate regions (i.e., machine vision). The automated system may then photopattern the substrate either subsequently or concurrently with the selection process. Of course, other computer systems, special purpose hardware, or the like could readily be substituted.

As noted above, the methods provided herein may be used in combination with various miniaturization and automation strategies. However, even the most sophisticated genetic testing methods will be of limited value if the input nucleic acids are not derived from pure populations of cells exhibiting the characteristic disease morphology. Accordingly, another application of the invention includes restricting the "active" surface of a DNA-chip to specific material in a sample. For example, body 40 and cover 46 of the reactor system might be formed by the DNA-chip itself, producing a narrow-spaced reaction chamber 42. Alternatively, the chip could function as substrate 20 with the biologic material established on surface 22 according to the present invention.

Further applications include providing the appropriate material for comparative genomic hybridization (CGH).

CGH is a method often confounded by excessive ratios of normal to abnormal cells (see Kallioniemi et al., Science 258:818, 1992). Still further applications include production of molecular electronic devices, and immobilization of labeled or unlabeled cells, proteins, antibodies, lectins, nucleic acids, nucleic acid probes, polysaccharides and the like in a pattern on a surface via molecular recognition of the exposed biologic material.

The following Examples are offered by way of illustration and not by way of limitation. Within these Examples, all operations were conducted at about ambient temperatures and pressures unless indicated to the contrary.

EXAMPLES

Example 1

Representative Regional Analysis of Biolouic Material

This Example illustrates the detection of specific nucleotide sequences in cancer cells.
A. Applying the Biologic Material to the Substrate Substrate surfaces containing either male lymphocytes, breast cancer cell lines, sections of normal breast tissue, or sections of breast cancer tissue were prepared as follows:

Breast cancer cell lines HTB131 and HTB129 (American Type Culture Collection, Rockville, Md.) were maintained as monolayer cultures in 75 $cm^2$ tissue culture flasks (Corning, N.Y.) in RPMI 1640 medium (Gibco BRL, Grand Island, N.Y.) supplemented with 6 mM L-glutamine, 10 $\mu$g/ml human insulin and 10% fetal calf serum, buffered with 14 mM sodium bicarbonate, 20 mM Hepes, and 20 $\mu$g/ml gentamicin. Cells were washed with 1×phosphate buffered saline (PBS) followed by incubation with 0.25% trypsin at 37° C. for 5 min. Cells were harvested from the flask, washed with 1×PBS, and resuspended in 1×PBS at a concentration range of $1\times10^6$ cells/ml to $9\times10^6$ cells/ml. Alternatively, peripheral male lymphocytes were obtained from peripheral blood using Ficoll-Paque® PLUS (Pharmacia, Uppsala, Sweden) according to the manufacturer's instructions, and resuspended in 1×PBS at a concentration range of $1\times10^6$ cells/ml to $9\times10^6$ cells/ml. Approximately 20 $\mu$l were taken from either the suspensions of breast cancer cells or male lymphocytes, and applied to a 1 $cm^2$ area of a standard, or positively-charged glass slide and allowed to air-dry. Positively-charged glass slides treated with aminopropyltrimethoxysilane were commercially obtained (Curtin-Matheson Scientific, Inc., Houston, Tex.). Occasionally, equal volumes (about 10 $\mu$l each) of breast cancer cells and male lymphocytes were intentionally applied to the same area of the slide. The cells were then hydrated with graded alcohols and subsequently stained with hematoxylin and eosin according to standard procedures generally known in the art. After staining with eosin, the cells were dehydrated in graded alcohols and allowed to air-dry.

Normal breast and breast cancer specimens from females were fixed in 10% buffered formalin and paraffin embedded according to tissue processing methods well known to those skilled in the art. From the paraffin embedded specimens, 5 $\mu$m thick sections were prepared using a standard tissue microtome, and placed on positively-charged glass slides. The sections were then subjected to deparaffinization with two, 10 minute washes with xylene. The sections were then hydrated with graded alcohols and subsequently stained with hematoxylin and eosin according to standard procedures. After staining with eosin, the sections were dehydrated in graded alcohols and allowed to air-dry.

Subsequent to air-drying, either the male lymphocytes, breast cancer cell lines, sections of normal breast tissue, or sections of breast cancer tissue were ready to be covered with photoresist.
B. Applying and Photopatterning the Photoresist While working in a laminar flow hood illuminated by cool-white fluorescent lights shielded with Gold Shields (Imtec Products Inc., Sunnyvale, Calif.), AZ® 1512 positive photoresist (Hoechst Celanese™, Somerville, N.J.) was applied without dilution to the surface of the biologic material described above using a Pasteur pipette. The excess was allowed to drain onto a paper towel by positioning the slide vertically. The slide was then placed on a flat surface for approximately 3 minutes at room temperature to partially evaporate the solvent, followed by soft-baking on a metal heating block at a temperature of from 90° C. to 100° C. for 1 to 2 minutes or in an oven at a temperature of from 90° C. to 100° C. for 15–30 minutes to completely evaporate the solvent. Partial evaporation of the solvent at room temperature prior to soft-baking was discovered to be critical for reproducibly achieving a photoresist layer of uniform thickness upon complete evaporation. The evaporated layer of photoresist was 5 $\mu$m to 10 m thick as determined by profilometry.

The slide was then transferred to the irradiation-targeting device illustrated in FIG. 8 and described above Light from long bandpass filter 214 transilluminated the substrate in area 228. Biologic material in area 228 was visualized through the translucent photoresist 30 using objective 208, microscope 206, and ocular optics 224. Specific regions of interest were located using x/y translation table 202 according to particular morphologic characteristics well recognized by those in the art. The regions of interest in the examples discussed herein consisted of lymphocytes, cells from a breast cancer cell line, breast epithelium, squamous epithelium, stroma, smooth muscle, lymphoid tissue, vasculature, glandular hyperplasia, ductal carcinoma in situ (DCIS, a pre-malignant condition), nests of primary breast cancer, and metastatic breast cancer.

Figure 9A:
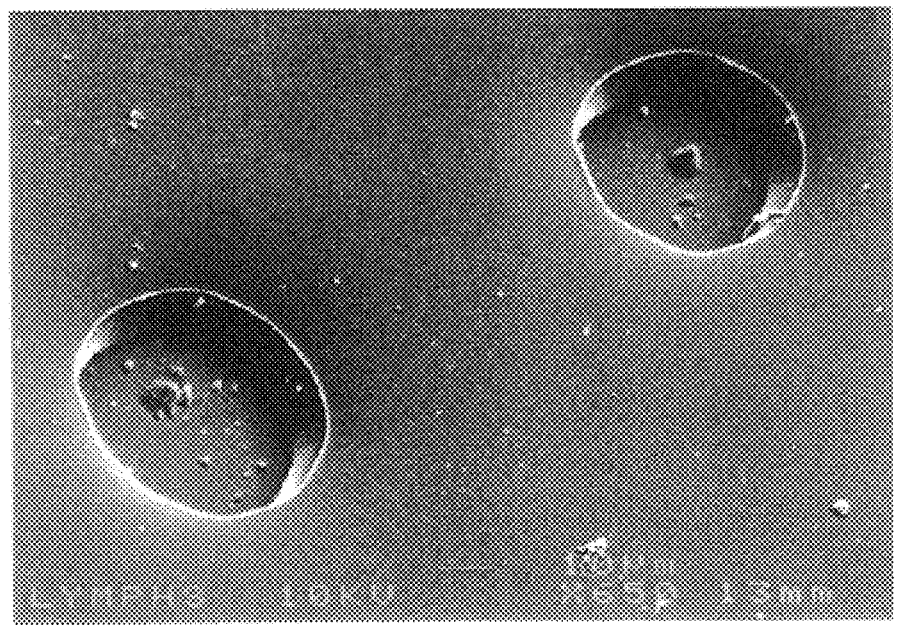
FIGS. 9A and 9B scanning electron microscope (SEM) prints of single exposed lymphocytes. The smaller debris are platelets.
Figure 9B:
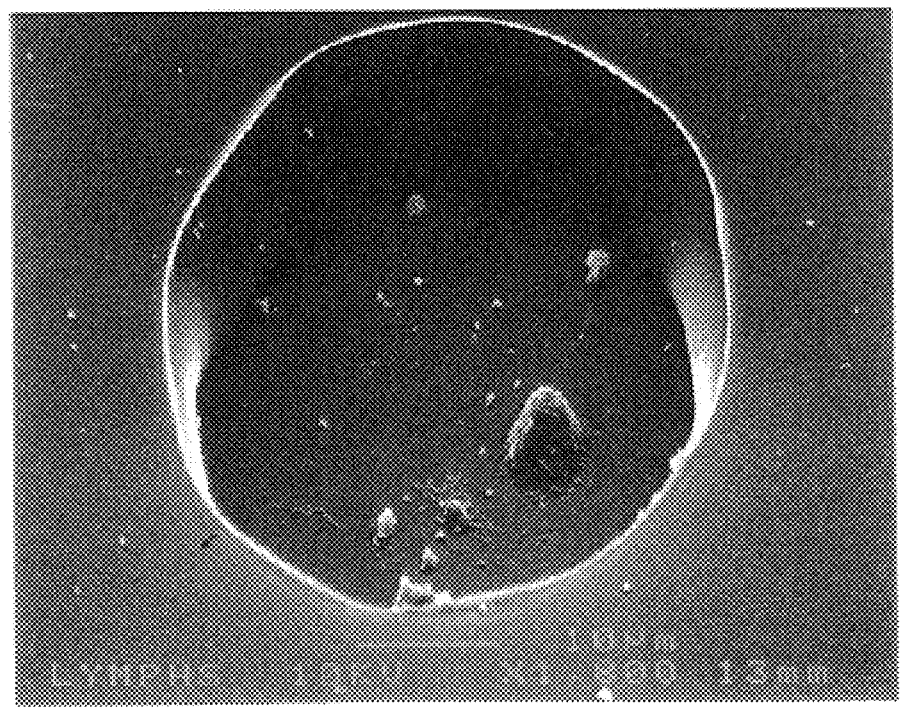

A region of interest was then positioned so that it encompassed area 226. If the region of interest was relatively large, area 226 was enlarged using iris diaphragm 218. Conversely, if the region of interest was relatively small, area 226 was decreased using iris diaphragm 218. With a region of interest appropriately in position, mechanical shutter 216 was opened allowing light from excitation filter 205 to epi-illuminate substrate 20 and photoresist 30 in area 226. Area 226 was visualized as a red fluorescent circle during epi-illumination. The temporal progress of the photochemical reaction was visualized by the formation of microscopic bubbles within photoresist 30 in area 226. The photochemical reaction was typically complete in 3 to 5 seconds with a 10× objective and a 50 Watt mercury lamp, and complete in less time with 20× and 40× objectives. The substrate was successively repositioned with shutter 216 open and iris diaphragm 218 appropriately re-adjusted until an entire region of interest was epi-illuminated. The substrate was then translated to a discontinuous region of interest with the shutter closed, and the above process repeated until all regions of interest were irradiated.
C. Developing the Photoresist and Applying the Reactor System With the photoresist appropriately photopatterned as described above, the entire substrate was immersed in AZ® 351 developer diluted six-fold with distilled water (Hoechst Celanese™, Somerville, N.J.). The photoresist in irradiated regions was completely dissolved after about 30 seconds in developer. The temporal progress of dissolution was visually monitored by the formation of red dye from irradiated regions during the development process. The dye is thought to form by the reaction of indene carboxylic acid (1V) with unreacted diazoquinone. After an additional 30 seconds in developer, the biologic material in irradiated regions lost both hematoxylin and eosin stains, appearing clear and translucent to the naked eye. After a total of 60 seconds in developer, the entire substrate was rinsed with distilled water three times, and allowed to air-dry. Examples of single exposed male lymphocytes using this process are depicted in the scanning electron print in FIG. 9 (smaller debris around larger single lymphocytes are platelets). Note the superior resolution and contrast (i.e., smooth borders that are sharp and steep between irradiated and unirradiated regions). Subsequent process steps were carried out under illumination with standard cool-white fluorescent lights A reactor system was formed with a nylon cylinder (Eagle Hardware, Seattle, Wash.) Mates to the photoresist surface with silicone adhesive (Dow-Corning, Midland, Mich.) as depicted in FIG. 7. The reactor system allowed for analysis of any exposed biologic material. Unexposed biologic material was blocked by a layer of photoresist and therefore could not be analyzed by the reactor system.

D Isolation of DNA From Irradiated Areas

Generally, DNA isolation is performed by the addition of a protease followed by extractions with organic solvents (e.g., phenol, chloroform) and precipitation with ethanol under conditions ,generally understood in the art. Although these methods are compatible with the invention as described herein, multiple purification steps increase the probability of losing DNA during the purification process. This is generally of little concern when samples contain many cells, but can be a significant limitation with samples containing only few cells (e.g., <1000). Examples herein were chosen to illustrate the superior capabilities of the invention by using samples containing from 1 to 1000 cells. Accordingly, a simplified DNA isolation method was devised which eliminates the organic solvent extractions and ethanol precipitation steps so as to minimize the probability of losing DNA during the purification process. An example of the purification method is as follows:

In general, the reactor cavity was filled with 100 μl of 100 mM Tris-HCl buffer at pH 8.0 containing 10 mM EDTA, and allowed to incubate for 1 hour. The reactor cavity was then rinsed twice with 100 μl of 100 mM Tris-HCl buffer at pH 8.0. This was followed by overnight incubation at 37° C. with 100 μl of "extraction solution" containing 50 mM Tris-HCl (pH 8.0), 1 mM EDTA, and 0.4 mg/ml to 1.0 mg/ml of proteinase K. After overnight incubation, the extraction solution was withdrawn from the reactor cavity and transferred to a 0.7 ml polypropylene tube. The extraction solution was then incubated at 80° C. for 30 minutes to heat denature the proteinase K while retaining DNA in the duplex form. The tube was then subjected to a brief centrifugation for 30 seconds to bring down any condensate. Aliquots of the extraction solution, as described, were then used in subsequent analytical methods (see examples below).

E. Specificity and Sensitivity

Specificity was demonstrated by applying a 50:50 mixture of male lymphocytes and HTB129 cells to three separate substrates according to "example A". Male lymphocytes and HTB129 cells contain 18 and 23 CAG repeats in the human androgen receptor gene, respectively. Each substrate was irradiated at either male lymphocytes, HTB129 cells, or male lymphocytes and HTB129 cells. Approximately 50 to 100 total cells were irradiated per substrate. Extraction solution was prepared for each irradiated substrate according to "examples C and D", and PCR amplified using primers which flank the CAG repeat as follows:

AR-F: 5'TCCAGAATCTGTTCCAGAGCGTGC 3' (SEQ ID NO:1)

AR-R: 5'GCTGTGAAGGTTGCTGTTCCTCAT 3' (SEQ ID NO:2)

DNA was also isolated from pure populations of male lymphocytes or HTB129 cells using, conventional methods (i.e., positive control DNA) and amplified using primers AR-F and AR-R. Amplification reactions consisted of the entire volume of extraction solution (or 100 ng of positive control DNA) in a total volume of 130 μl containing 1 μM AR-F and AR-R primers, 250 μM dNTPs (Boehringer Mannheim, Indianapolis, Ind.), 3.0 U Taq polymerase (Boehringer Mannheim, Indianapolis, Ind.), 5.0 μCi alpha-$^{32}$P-dCTP (New England Nuclear, Boston, Mass.), 1.5 mM $MgCl_2$, 50 mM KCl, and 50 mM Tris-HCl (pH 8.3). Amplification was performed using an automated thermocycler (Perkin-Elmer, Branchburg, N.J.) for 40 cycles (cycle=60s @ 94° C., 75s @ 61°C., 75s @ 72° C.), followed by a 72° C. soak for 10 min. Reactions without added DNA were included as negative controls.

A 4 μl aliquot of each sample was combined with an equal volume of loading buffer containing 98% deionized formamide, 10 mM EDTA, 0.2% xylene cyanol, and 0.2% bromophenol blue followed by denaturation at 94° C. for 2 min. Amplification products were separated by electrophoresis for 2–3 hours at 65 Watts constant power in a 5% polyacrylamide gel containing 7 M urea, 100 mM Tris borate (pH 8.9), and 1 mM EDTA. The gel was dried onto 3 mm paper (Whatman) and autoradiographed overnight at −70° C. on XAR-5 film (Kodak) with an intensifying screen. Product lengths were determined by comparison with an external size standard or by direct DNA sequencing.

Bands from the autoradiographed gel are depicted in FIG. 10. The product containing the greater number of trinucleotide repeats had a slower mobility because it was larger. Doublet bands were produced because each denatured strand had a slightly different mobility. The "+" symbols in each lane indicate which cells DNA is purified from and the purification method used. Lanes 4 and 5 represent the positive controls (i.e., DNA isolated from pure populations of lymphocytes or HTB129 cells using conventional methods). As expected, PCR of male lymphocyte DNA resulted in the $(CAG)_{18}$ product (lane 4), and PCR of HTB129 DNA results in the $(CAG)_{23}$ product (lane 5). Lanes 1 through 3 represent each of the three substrates prepared as described above. The substrate irradiated at both male lymphocytes and HTB129 cells resulted in both $(CAG)_{18}$ and $(CAG)_{23}$ products (lane 1). In contrast, substrates irradiated at either male lymphocytes (lane 2) or HTB129 cells (lane 3) demonstrate the exquisite specificity of the invention. In these cases, amplification products were essentially 100% specific to the irradiated cells. That is, irradiation of male lymphocytes resulted in the $(CAG)_{18}$ product (lane 2), and irradiation of HTB129 cells results in the $(CAG)_{23}$ product. There was no evidence of amplification products from unirradiated cells even upon prolonged exposure of the gel to film for one week.

This was corroborated by directly examining the substrate as shown in FIG. 11. The left panel shows irradiated regions of destained, male lymphocytes prior to the addition of extraction solution containing proteinase K. The right panel shows that the irradiated cells are absent after the addition of extraction solution, and that cells in unirradiated regions are unaltered. Furthermore, this is apparent even in cells as close as 1–5 μm from an irradiated region.

Sensitivity was demonstrated by applying male lymphocytes to five substrates prepared according to subpart A, above. Irradiations of 50, 20, 5, 1 and 0 male lymphocytes were performed separately on each of the five substrates. Extraction solution was prepared for each irradiated substrate according to subpart D, above. Each extraction solution was PCR amplified, electrophoresed, and autoradiographed according to the above methods, except that the get was autoradiographed for 5 days The autoradiograph is depicted in FIG. 12. Amplification product was visualized from as few as 5 irradiated lymphocytes. This demonstrates that the invention has exquisite sensitivity equivalent to the limit of PCR detection.

Example 2

Representative Regional Analysis of Methylated DNA

This Example illustrates the capability of the present invention to detect methylated DNA compositions from minute regions of normal and cancerous tissues using site-specific DNA cleavage. As previously note by Lyon, only one of two X chromosomes is active in a somatic female cell with the inactive X chromosome methylated at CG sequences (Lyon, *Biol. Rev.* 47:1, 1972). Inactivation is a random event occurring early in embryo genesis resulting in inactivation of either the maternal or paternal X chromosome. Thus, normal female tissue is a mosaic, consisting of clusters of maternally inactivated cells adjacent to clusters of paternally inactivated cells. The size of a cluster, or "patch" is not completely known. The somatic mutation theory of carcinogenesis states that a malignant neoplasm represents the clonal expansion of a single mutated somatic cell that acquired a selective growth advantage over its normal counterparts. Such clones will all maintain the same X inactivation pattern as the patch from which they arose.

Figure 13:
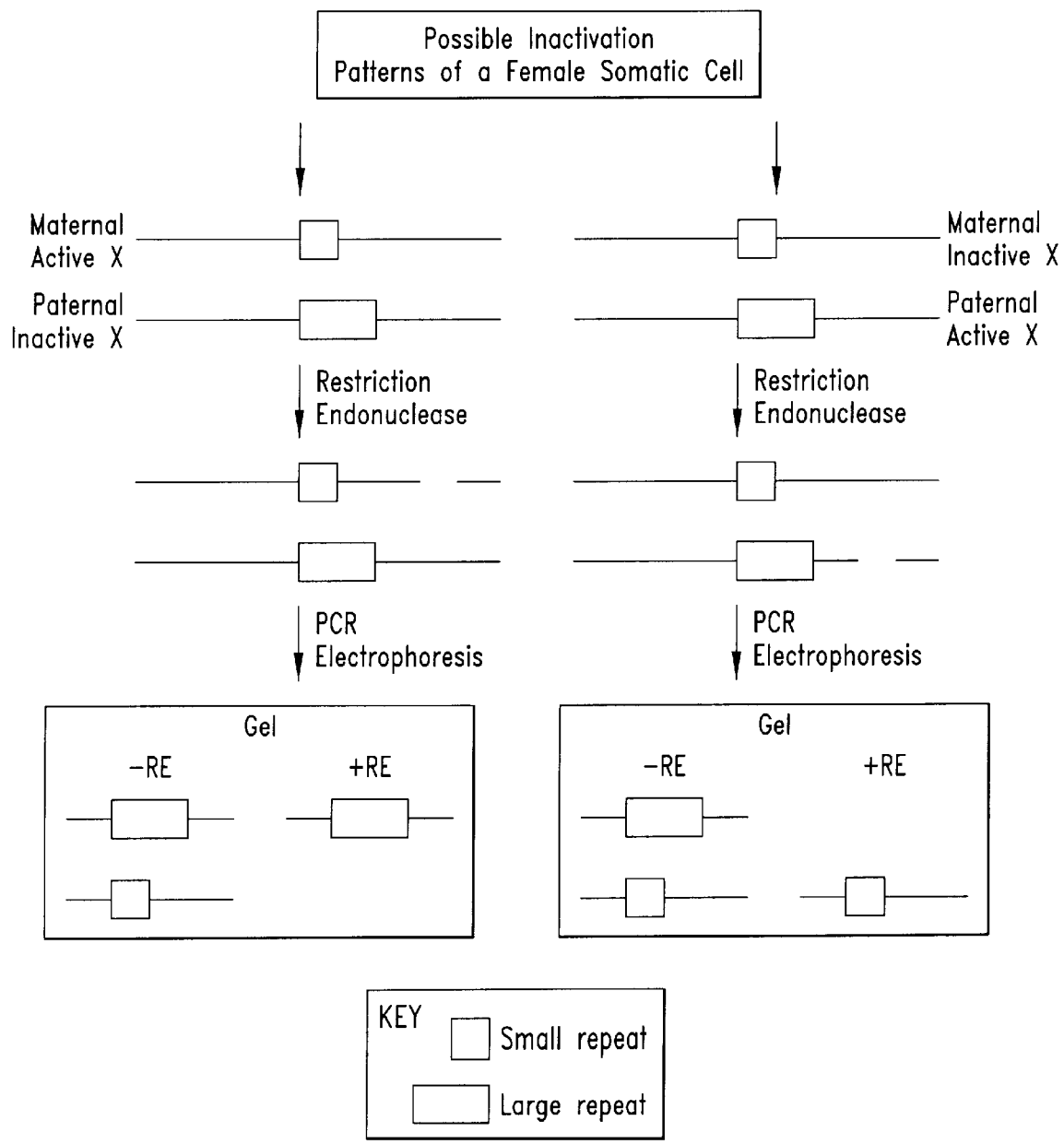
FIG. 13 is a flow chart of an assay to detect the X inactivation pattern in a population of cells according to a prior art method.

Methylation patterns of the X chromosome were detected essentially as described by Allen, et al., *Am. J. Hum. Genet.* 51:1229, 1992. With reference to FIG. 13, a female somatic cell methylates either the maternal or paternal androgen receptor gene (located at Xq13). The trinucleotide repeat in the coding region of the androgen receptor gene consists of 20 alleles ranging from 11 to 31 repeats with 92% heterozygosity. PCR with primers flanking the polymorphic repeat will amplify both alleles (see Example 1, subpart E). This may be seen as two bands after electrophoresis (see "–RE" lanes in FIG. 13 where "–RE" =no restriction enzyme present) However, if the DNA is digested with methylation-sensitive restriction enzymes prior to PCR, the unmethylated template is cleaved and amplification occurs only from the methylated allele (see "+RE" lanes in FIG. 13 where "+RE" =restriction enzyme present).

Normal tissue generally results in amplification of both maternal and paternal alleles because half of the patches contain a methylated maternal allele and half contain a methylated paternal allele (i.e., a polyclonal pattern). This is seen as two bands after get electrophoresis (both +RE lanes in FIG. 13 superimposed). Methylation patterns have not previously been established from single patches. A pure malignant population will produce only one of two bands because the same methylation pattern is maintained in all malignant cells.

Accordingly, 5 μm thick paraffin embedded sections were applied to substrates as described above. Specific regions of interest were located and irradiated as described above using morphologic characteristics well recognized by those in the art. Regions of interest in this example were breast epithelium, squamous epithelium, smooth muscle, lymphoid tissue, vasculature, ductal carcinoma in situ (DCIS, a pre-malignant condition), and nests of primary breast cancer. When cancer cells were targeted, normal tissues found in cancer such a vasculature, stroma and inflammatory cells were carefully avoided so as to obtain DNA from cancer cells only. From 50 to 500 total cells were irradiated per substrate. Extraction solution was prepared from each irradiated substrate as described above. For each extraction solution, a reaction without (i.e., —RE) and with (i.e., +RE) restriction enzymes was prepared consisting of 20 μl of extraction solution in a total volume of 26 μl containing 56 mM Tris-HCl (pH 8.3), 2.6 mM MgCl2, and 10 units each of CfoI and HpaII in the +RE reaction. CfoI and HpaII restriction enzymes will not cleave DNA containing CG sequences methylated at cytosine position 5. All reactions were incubated for 5 hours at 37° C., followed by heat inactivation of the restriction enzymes at 65° C. for 10 min.

The entire –RE and +RE reactions were amplified in a total volume of 33 μl containing 1 μM AR-F and AR-R primers, 250 μM dNTPs (Boehringer Mannheim, Indianapolis, Ind.), 2.5 U Taq polymerase (Boehringer Mannheim, Indianapolis, Ind.), 4.0 μCi alpha-$^{32}$P-dCTP (New England Nuclear, Boston, Mass.), 1.5 mM MgCl$_2$, 50 mM KCl, and 95 mM Tris-HCl (pH 8.3). Amplification was performed using an automated thermocycler (Perkin-Elmer, Branchburg, N.J.) for 40 cycles (cycle =60s @ 94° C., 75s @61° C., 75s @ 72° C.), followed by a 72° C. soak for 10 min. Reactions without added DNA were included as negative controls.

A 4 μl aliquot of each sample was combined with an equal volume of loading buffer containing 98% deionized formamide, 10 mM EDTA, 0.2% xylene cyanol, and 0.2% bromophenol blue followed by denaturation at 94° C. for 2 min. Amplification products were separated by electrophoresis for 2–3 hours at 65 Watts constant power in a 5% polyacrylamide get containing 7 M urea, 100 mM Tris borate (pH 8.9), and 1 mM EDTA. Amplification products from each extraction solution were loaded on the get as –RE and +RE pairs. The gel was dried onto 3 mm paper (Whatman) and autoradiographed overnight at –70° C. on XAR-5 film (Kodak) with an intensifying screen.

Figure 14A:
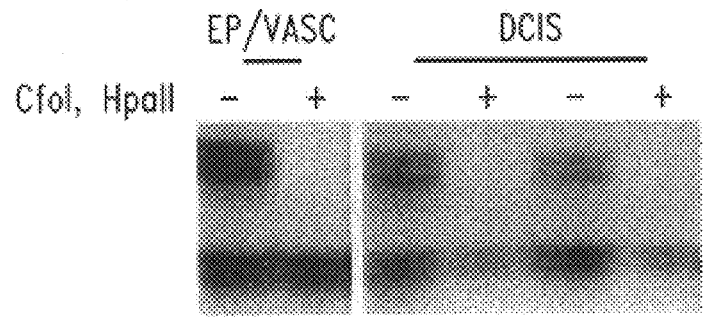
FIGS. 14A and 14B are autoradiograms demonstrating the detection of methylation patterns of the X chromosome in normal and cancerous tissues.
Figure 14B:
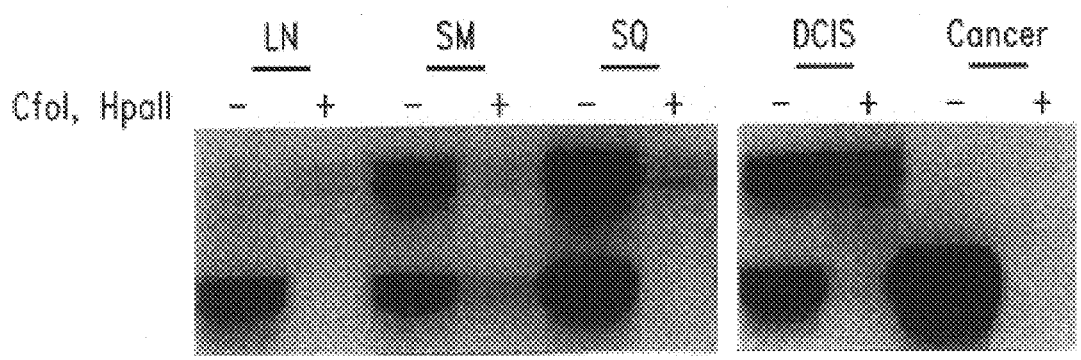

Using the resolution capabilities of the present invention, the methylation pattern of single patches were examined. The results from breast cancer cases 3413 and 2767 are depicted in FIG. 14 where the symbols "–" =–RE, and "+"+RE. Normal tissues were found to have a monoclonal methylation pattern when irradiated in sufficiently small regions encompassing a single patch. For example, the gland epithelium ("EP") and vasculature ("VASC") in case 3413, and the lymph node ("LN") and squamous epithelium ("SQ") in case 2767 all had a monoclonal methylation pattern. However, when the irradiated region was expanded to encompass more than one patch, a polyclonal pattern was found as in the smooth muscle ("SM") in case 2767.

Separate irradiated regions of DCIS were found to have monoclonal methylation patterns in both cases. Identical methylation patterns in case 3413 are expected based on the somatic mutation theory of carcinogenesis. The cancer in case 2767 illustrates loss of genetic material which often occurs in the stepwise progression of cancer. In this case, the androgen receptor gene was deleted from the inactive X chromosome. These examples demonstrate that the invention produces DNA which was completely and site-specifically cleaved from a range of cell types and cell numbers, as evidenced by absent amplification of the unmethylated allele after restriction enzyme digestion.

Figure 15:
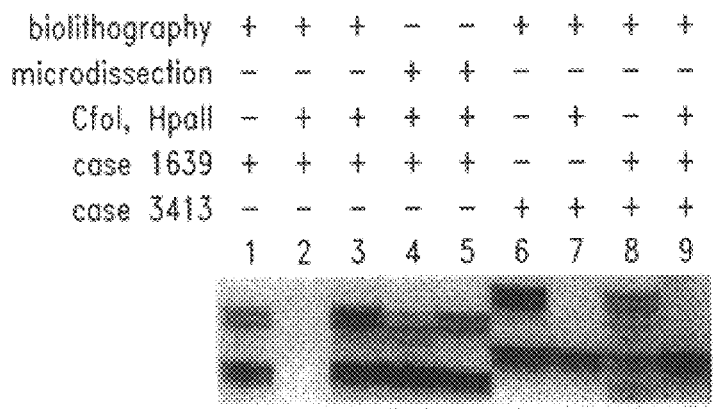
FIG. 15 is an autoradiogram demonstrating the detection of demethylation in a cancerous tissue, and the inability to detect the same demethylation according to a prior art method (i.e., microdissection). The "+" symbols in each lane indicate which cells DNA was purified from, the purification method used and the presence or absence of methylation-sensitive restriction enzymes.

In some cases of DCIS and breast cancer it was discovered that neither X chromosome was methylated. With reference to FIG. 15, two alleles were amplified from the cancer in case 1639 (lane 1), but upon restriction enzyme digestion, neither allele was amplified (lane 2). To test for the possibility of a PCR inhibitor, 8 µl of extraction solution was added to 18 µl of the heat inactivated restriction enzyme digest prior to PCR amplification. No PCR inhibitor was detected as both alleles amplified (lane 3). To test more generally for the presence of diffusible inhibitors or degradative enzymes, extraction solution from the cancer in case 3413 was added as an internal control. The cancer in case 3413 contained a monoclonal methylation pattern (compare lanes 6 and 7). Equal volumes of extraction solution from cases 1639 and 3413 were combined, and in the absence of restriction enzymes all four alleles amplified (lane 8). In the presence of restriction enzymes, only the allele from case 3413 amplified (lane 9). The lack of allele amplification from case 1639 upon restriction enzyme digestion is therefore due to absent methylation rather than a diffusible factor.

Absent X chromosome methylation in case 1639 was not detected using a microdissection technique described in the prior art (see Emmert-Buck et al., *Am. J. Pathol.* 145:1285, 1994; Zhuang et al., *Am. J. Pathol.* 146:620, 1995 and Noguchi et al., *Cancer Res.* 54:1849, 1994). Two microdissection efforts each resulted in a polyclonal methylation pattern (lanes 4 and 5). Polyclonal tissues inter-mixed with cancer cells such a vasculature and lymphocytes were difficult to avoid using microdissection, and probably accounted for the erroneous result.

Figure 16:
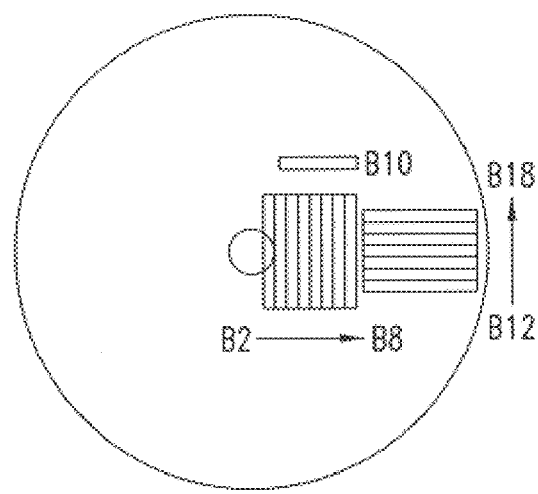
FIG. 16 is an autoradiogram demonstrating the detection of methylation patterns as a function of position within a tumor. For each lane, the position examined is indicated relative to the accompanying diagram. In each case, incubation with methylation-sensitive restriction enzymes is indicated by the "+."
Figure 16:
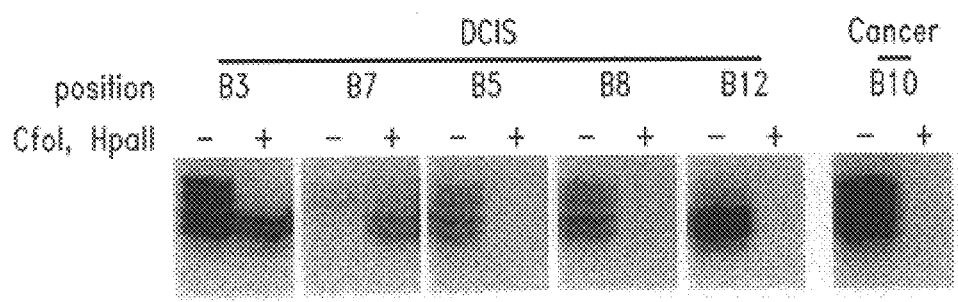

In another case, demethylation was spatially examined as depicted in FIG. 16. The evolution of demethylation, and deletion of genetic material correlated with position in the subject's breast. The DCIS appeared to have started with a monoclonal methylation pattern (B3, B7) followed by demethylation (B5, B8) and eventually deletion of genetic material peripherally (B12). The cancer presumably arose as a subclone of the intermediate, demethylated stage (B10). These results suggest demethylation of the X chromosome may be involved in the stepwise progression of breast cancer. It is likely that understanding other position-composition relationships will further our understanding of carcinogenesis in a variety of tumors.

Accordingly, these Examples demonstrate the detection of highly accurate position-composition relationships using analytic methods and the methods provided herein. Superior resolution, contrast, and selection accuracy allowed detection of methylation patterns in single mosaic patches, and the discovery of a potentially novel mechanism of carcinogenesis involving demethylation of the X chromosome.

Example 3

Detection of Lost Genetic Material: Microsatellite Analysis

This Example illustrates the capability of the present invention to detect deleted DNA compositions from minute regions embedded in normal tissue. Functional loss of essential tumor suppressors is a key mechanism in the stepwise progression of cancer. Loss usually occurs by deletion of at least one tumor suppressor gene together with megabases of adjacent DNA. Deletion of the tumor suppressor gene may be indirectly detected using a linked microsatellite marker. Microsatellites are polymorphic markers containing a variable number of repeats. Marker heterozygosity occurs when maternal and paternal alleles have a different number of repeats. Loss of heterozygosity (LOH) is seen when a tumor suppressor gene is deleted together with the adjacent microsatellite marker, and the cell is left with a single microsatellite allele. Occasionally, a homozygous deletion occurs, leaving no alleles.

An obstacle to identifying LOH is the fact that tumors are heterogeneous, containing tumor cells and various normal cells. DNA from homogenized tumor samples reflects the average content of all cell types present in the sample; abnormal and normal. The presence of genetic material from contaminating normal cells often obscures LOH. As such, the prior art recognizes the need to isolate tumor cells away from normal cells before a microsatellite analysis is applied. The invention as described herein satisfies this need, providing for the routine detection of LOH directly from tumors. In the following example, LOH was detected in several paraffin-embedded breast cancers using the invention, and a PCR method generally understood in the art.

Five µm thick paraffin-embedded sections were applied to substrates as described above. Specific regions of interest were located and irradiated as described above using morphologic characteristics well recognized by those in the art. Regions of interest in this example were glandular breast epithelium, squamous epithelium, vasculature, ductal carcinoma in situ (DCIS, a pre-malignant condition), and nests of primary breast cancer. From 50 to 500 total cells were irradiated per substrate. Extraction solution was prepared from each irradiated substrate as described above, and categorized as either normal ("N"), DCIS ("D"), or cancer ("C").

For each microsatellite marker, two PCR assays were prepared using "N" and "C" extraction solutions. Occasionally, a PCR assay was also prepared using "D" extraction solution. Primers flanking each microsatellite marker were commercially obtained (MapPairs™, Research Genetics, Huntsville, Ala.). For each PCR assay, a 5 µl aliquot of extraction solution was amplified in a total reaction volume of 15 µl containing 1 µM primers, 250 µM dNTPs (Boehringer Mannheim, Indianapolis, Ind.), 1.2 U Taq polymerase (Boehringer Mannheim, Indianapolis, Ind.), 3.0 µCi alpha-$^{32}$P-dCTP (New England Nuclear, Boston, Mass.), 1.5 mM MgCl$_2$, 50 mM KCl, and 50 mM Tris-HCl (pH 8.3). Amplification was performed using an automated thermocycler (Perkin-Elmer, Branchburg, N.J.) for 40 cycles (cycle =60s @ 94° C., 60s @55° C., 60s @ 72° C.), followed by a 72° C. soak for 10 min.

A 4 µl aliquot of each sample was combined with an equal volume of loading buffer containing 98% deionized formamide, 10 mM EDTA, 0.2% xylene cyanol, and 0.2% bromophenol blue followed by denaturation at 94° C. for 2 min. Amplification products were separated by electrophoresis for 2–3 hours at 65 Watts constant power in a 5% polyacrylamide gel containing 7 M urea, 100 mM Tris borate (pH 8.9), and 1 mM EDTA. Amplification products for each microsatellite marker were loaded on the gel as "N", "C" or "N", "D", "C" groups. The gel was dried onto 3 mm paper (Whatman) and autoradiographed overnight at −70° C. on XAR-5 film (Kodak) with an intensifying screen. Heterozygous amplification products were visualized on the autoradiograph as two dominant bands with different mobility. LOH was present when one of the heterozygous amplification products in the "N" lane was missing in the "D" or "C" lanes. Abnormal priming of the polymerase accounts for minor amplification products as previously documented in the art.

Figure 17:
FIG. 17 is an autoradiogram demonstrating a microsatellite analysis of a cancer according to the present invention. Cells were characterized as normal (N) or cancer (C) as indicated. In each case, PCR analyses were performed for the indicated microsatellite marker for the following genes: DNA methyltransferase (DNMT), the methyl CG binding protein 2 (MECP2), the X inactive specific transcript (XIST), and a cytogenetic region involved in choosing which X chromosome is inactivated (Xq27.3).
Figure 18:
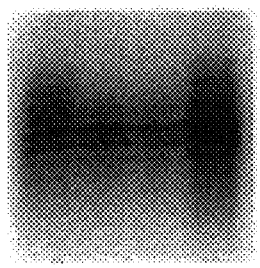
FIG. 18 is an autoradiogram demonstrating a microsatellite analysis (LOH at DXS8092) of a cancer according to the present invention and a prior art method (i.e., microdissection). The "+" symbols in each lane indicate the purification method used. Cells were characterized as normal (N) or cancer (C) as indicated.

The results from breast cancer case 1639 are depicted in FIG. 17. Markers linked to genes involved in the X inactivation process were chosen to potentially define the genetic basis for demethylation of the X chromosome. These genes included the DNA methyltransferase (DNMT), the methyl CG binding protein 2 (MECP2), the X inactive specific transcript (XIST), and a cytogenetic region involved in choosing which X chromosome is inactivated (Xq27.3). There was no evidence of LOH at any of the markers except DXS8092. Using the invention described herein, LOH at the DXS8092 marker was repeated twice as depicted in FIG. 18 (center two lanes). However, LOH at DXS8092 was not detected using a microdissection technique from the prior art (see above). Polyclonal tissues inter-mixed with cancer cells such as vasculature and lymphocytes were difficult to avoid using microdissection probably accounting for the inability to detect LOH.

Figure 19:
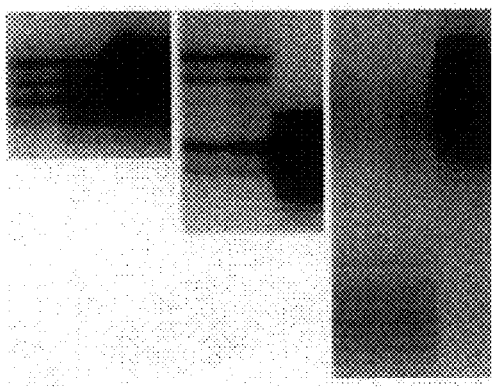
FIG. 19 is an autoradiogram demonstrating a microsatellite analysis of DCIS and cancer according to the present invention. Cells were characterized as normal (N), DCIS (D) or cancer (C) as indicated. In each case, PCR analyses were performed for the indicated microsatellite marker for the methyl CG binding protein 2 (MECP2) and a cytogenetic region involved in choosing which X chromosome is inactivated (Xq27.3).

Examples of LOH in case 2767 are depicted in FIG. 19. Notably, the invention provides the ability to document lost genetic material in the cancer that is present in the precursor lesion (i.e., DCIS). Such relationships help define carcinogenic pathways at the genetic level. In total, over 300 microsatellite analyses have been performed using the invention. This example demonstrates the general ability of the method to effectively isolate tumor cells from normal cells so that analytic methods successfully detect deleted genetic material. The example also demonstrates a method to precisely define position-composition relationships over a broad range of normal tissues, precursors, and tumors.

From the foregoing, it will be appreciated that, although specific embodiments of the invention have been described herein for the purpose of illustration, various modifications may be made without deviating from the spirit and scope of the invention. Accordingly, the present invention is not limited except by the appended claims.

What is claimed is:

1. A method for analyzing a discrete region of a biologic material, comprising the steps of:
   (a) irradiating photoresist coated on a first region of a biologic material, wherein the biologic material is immobilized on a substrate, such that:
      (i) photoresist coated on the first region is substantially removed and photoresist coated on a second region of the biologic material is not substantially removed, resulting in exposed biologic material in the first region; or
      (ii) photoresist coated on a second region is substantially removed and photoresist coated on the first region of the biologic material is not substantially removed, resulting in exposed biologic material in the second region; and
   (b) determining the presence or absence of a substance of interest in the exposed biologic material; and therefrom analyzing a discrete region of the biologic material for the presence or absence of a substance of interest.

2. A method according to claim 1, wherein the photoresist comprises a polyphenolformaldehyde polymer and a diazoquinone.

3. A method according to claim 1, wherein step (b) comprises the steps of:
   (i) contacting the exposed biologic material with a detection reagent that generates a detectable response indicative of the presence or absence of a substance of interest in the exposed biologic material; and
   (ii) detecting a response generated by the detection reagent.

4. A method according to claim 3, wherein the detection reagent comprises an antibody, nucleic acid sequence or enzyme.

5. A method according to claim 3, wherein the detection reagent comprises a marker.

6. A method according to claim 5, wherein the marker is a chromophor, fluorophor or radionuclide.

---

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Primer for PCR Amplification

<400> SEQUENCE: 1
tccagaatct gttccagagc gtgc                                    24

<210> SEQ ID NO 2
<211> LENGTH: 24
<212> TYPE: DNA
<213> ORGANISM: Artificial Sequence
<220> FEATURE:
<223> OTHER INFORMATION: Primer for PCR Amplification

<400> SEQUENCE: 2
gctgtgaagg ttgctgttcc tcat                                    24

7. A method according to claim 1, wherein step (b) comprises an assay selected from the group consisting of electrophoresis, chromatography, mass spectrometry, DNA sequencing, peptide sequencing nucleic acid hybridization and PCR.

8. A method according to claim 1, wherein the step of irradiating further comprises contacting the photoresist with a developer.

9. A method according to claim 1, wherein photoresist is removed from at least 100 discrete regions.

10. A method according to claim 1, wherein photoresist is removed from at least 10,000 discrete regions.

11. A method according to claim 1, wherein the first and second regions each have an area of less than 10,000 square microns.

12. A method according to claim 1, wherein the first and second regions each have an area of less than 100 square microns.

13. A method according to claim 1, wherein the first and second regions each have an area of less than 1 square micron.

14. A method according to claim 1, wherein the substrate comprises a material selected from the group consisting of glass, germanium, silicon, silicon nitride, silicon oxide, gallium phosphide, gallium arsenide, polystyrene, (poly) tetrafluorethylene.

15. A method according to claim 1, wherein the biologic material is immobilized on the substrate via a linker.

16. A method according to claim 1, wherein the irradiation is selected from the group consisting of coherent light, incoherent light, x-ray light, ultraviolet light, visible light and infrared light.

17. A method according to claim 1, wherein the biologic material comprises one or more biological tissues, cells or viruses.

18. A method according to claim 1, wherein the biologic material comprises at least one compound selected from the group consisting of nucleic acid molecules, peptide nucleic acids, proteins, peptides, polysaccharides, monosaccharides, lectins and lipids.

19. A method according to claim 1, wherein the substance of interest is a cell or virus.

20. A method according to claim 1, wherein the substance of interest is a compound selected from the group consisting of nucleic acid molecules, proteins, peptides, polysaccharides, monosaccharides, lectins and lipids.

21. A method according to claim 1, wherein prior to or concurrently with the step of irradiation, the photoresist is illuminated with a light that does not substantially react with the photoresist.

22. A method according to claim 1, wherein the first region is irradiated by:
(i) placing a mask between the photoresist and a source of irradiation, wherein the mask has at least one region that is substantially transparent to the irradiation and at least one region that is substantially opaque to the irradiation; and
(ii) irradiating the mask with the irradiation such that irradiation passes through the mask to photoresist coated on the first region.

23. A method for analyzing a discrete region of a biologic material, comprising the steps of:
(a) irradiating photoresist coated on a first region of a biologic material, wherein the biologic material is immobilized on a substrate, such that:
(i) photoresist coated on the first region is substantially removed and photoresist coated on a second region of the biologic material is not substantially removed, resulting in exposed biologic material in the first region; or
(ii) photoresist coated on a second region is substantially removed and photoresist coated on the first region of the biologic material is not substantially removed, resulting in exposed biologic material in the second region;
(b) contacting the exposed biologic material with an ablative agent, such that a substance of interest is not detectable in the exposed biologic material;
(c) substantially removing remaining photoresist, exposing remaining biologic material; and
(d) determining the presence or absence of a substance of interest in the remaining biologic material; and therefrom analyzing a discrete region of the biologic material for the presence or absence of a substance of interest.

24. A method according to claim 23, wherein the ablative agent is selected from the group consisting of oxidants, free radicals, non-specific nucleases, non-specific ribonucleases, peptide nucleic acid clamps, high energy particles, extremes of radiation, ultraviolet irradiation and combinations thereof.

25. A method according to claim 23, wherein the photoresist comprises a polyphenolformaldehyde polymer and a diazoquinone.

26. A method according to claim 23, wherein step (b) comprises the steps of:
(i) contacting the exposed remaining biologic material with a detection reagent that generates a detectable response indicative of the presence or absence of a substance of interest in the exposed remaining biologic material; and
(ii) detecting a response generated by the detection reagent.

27. A method according to claim 26, wherein the detection reagent comprises an antibody, nucleic acid sequence or enzyme.

28. A method according to claim 26, wherein the detection reagent comprises a marker.

29. A method according to claim 28, wherein the marker is a chromophor, fluorophor or radionuclide.

30. A method according to claim 23, wherein step (b) comprises an assay selected from the group consisting of electrophoresis, chromatography, mass spectrometry, DNA sequencing, peptide sequencing, nucleic acid hybridization and PCR.

31. A method according to claim 23, wherein the step of irradiating further comprises contacting the photoresist with a developer.

32. A method according to claim 23, wherein photoresist is removed from at least 100 discrete regions.

33. A method according to claim 23, wherein photoresist is removed from at least 10,000 discrete regions.

34. A method according to claim 23, wherein the first and second regions each have an area of less than 10,000 square microns.

35. A method according to claim 23, wherein the first and second regions each have an area of less than 100 square microns.

36. A method according to claim 23, wherein the first and second regions each have an area of less than 1 square micron.

37. A method according to claim 23, wherein the substrate comprises a material selected from the group consisting of glass, germanium, silicon, silicon nitride, silicon oxide, gallium phosphide, gallium arsenide, polystyrene, (poly) tetrafluorethylene.

38. A method according to claim 23, wherein the biologic material is immobilized on the substrate via a linker.

39. A method according to claim 23, wherein the irradiation is selected from the group consisting of coherent light, incoherent light, x-ray light, ultraviolet light, visible light and infrared light.

40. A method according to claim 23, wherein the biologic material comprises one or more biological tissues, cells or viruses.

41. A method according to claim 23, wherein the biologic material comprises at least one compound selected from the group consisting of nucleic acid molecules, peptide nucleic acids, proteins, peptides, polysaccharides, monosaccharides, lectins and lipids.

42. A method according to claim 23, wherein the substance of interest is a cell or virus.

43. A method according to claim 23, wherein the substance of interest is a compound selected from the group consisting of nucleic acid molecules, proteins, peptides, polysaccharides, monosaccharides, lectins and lipids.

44. A method according to claim 23, wherein prior to or concurrently with the step of irradiation, the photoresist is illuminated with a light that does not substantially react with the photoresist.

45. A method according to claim 23, wherein the first region is irradiated by:
 (i) placing a mask between the photoresist and a source of irradiation, wherein the mask has at least one region that is substantially transparent to the irradiation and at least one region that is substantially opaque to the irradiation; and
 (ii) irradiating the mask with the irradiation such that irradiation passes through the mask to photoresist coated on the first region.

46. A method for analyzing a discrete region of a biologic material, comprising the steps of:
 (a) irradiating positive photoresist coated on a first region of a biologic material, wherein the biologic material is immobilized on a substrate, such that photoresist coated on the first region is substantially removed and photoresist coated on a second region of the biologic material is not substantially removed, resulting in exposed biologic material in the first region; and
 (b) determining the presence or absence of a substance of interest in the exposed biologic material; and therefrom analyzing a discrete region of the biologic material for the presence or absence of a substance of interest.

47. A method for analyzing a discrete region of a biologic material, comprising the steps of:
 (a) irradiating negative photoresist coated on a first region of a biologic material, wherein the biologic material is immobilized on a substrate, and wherein the step of irradiating comprises contacting photoresist on at least a second region of the biological material with a developer such that photoresist coated on the second region is substantially removed and photoresist coated on the first region is not substantially removed, resulting in exposed biologic material in the second region; and
 (b) determining the presence or absence of a substance of interest in the exposed biologic material; and therefrom analyzing a discrete region of the biologic material for the presence or absence of a substance of interest.

48. A method for analyzing a discrete region of a biologic material, comprising the steps of:
 (a) irradiating positive photoresist coated on a first region of a biologic material, wherein the biologic material is immobilized on a substrate, such that photoresist coated on the first region is substantially removed and photoresist coated on a second region of the biologic material is not substantially removed, resulting in exposed biologic material in the first region;
 (b) contacting the exposed biologic material with an ablative agent, such that a substance of interest is not detectable in the exposed biologic material;
 (c) substantially removing remaining photoresist, exposing remaining biologic material; and
 (d) determining the presence or absence of a substance of interest in the remaining biologic material; and therefrom analyzing a discrete region of the biologic material for the presence or absence of a substance of interest.

49. A method for analyzing a discrete region of a biologic material, comprising the steps of:
 (a) irradiating negative photoresist coated on a first region of a biologic material, wherein the biologic material is immobilized on a substrate, and wherein the step of irradiating comprises contacting photoresist on at least a second region of the biological material with a developer such that photoresist coated on the second region is substantially removed and photoresist coated on the first region is not substantially removed, resulting in exposed biologic material in the second region;
 (b) contacting the exposed biologic material with an ablative agent, such that a substance of interest is not detectable in the exposed biologic material;
 (c) substantially removing remaining photoresist, exposing remaining biologic material; and
 (d) determining the presence or absence of a substance of interest in the remaining biologic material; and therefrom analyzing a discrete region of the biologic material for the presence or absence of a substance of interest.

* * * * *

UNITED STATES PATENT AND TRADEMARK OFFICE
CERTIFICATE OF CORRECTION

| | | |
|---|---|---|
| PATENT NO. | : 6,159,681 | Page 1 of 1 |
| APPLICATION NO. | : 09/322060 | |
| DATED | : December 12, 2000 | |
| INVENTOR(S) | : John A. Zebala | |

It is certified that error appears in the above-identified patent and that said Letters Patent is hereby corrected as shown below:

Col. 1, line 21, insert a Government Rights Statement as shown below:

--This invention was made with government support under Grant Number DAMD17-96-1-6120 awarded by the U.S. Army Medical Research and Materiel Command. The government has certain rights to this invention.--

Signed and Sealed this
Eighteenth Day of December, 2012

David J. Kappos
*Director of the United States Patent and Trademark Office*